(12) United States Patent
Gamolski

(10) Patent No.: US 11,203,760 B2
(45) Date of Patent: Dec. 21, 2021

(54) GENE THERAPY DNA VECTOR GDTT1.8NAS12 AND THE METHOD FOR OBTAINING THEREOF

(71) Applicants: GENETIC DIAGNOSTICS AND THERAPY 21 LTD, London (GB); Obschestvo s ogranichennoi otvetstvennostju «REKOMBITEKH», Moscow (RU)

(72) Inventor: Anton Gamolski, London (GB)

(73) Assignees: GENETIC DIAGNOSTICS AND THERAPY 21 LTD, London (GB); Obschestvo s ogranichennoi otvetstvennostju «REKOMBITEKH», Moscow (RU)

( * ) Notice: Subject to any disclaimer, the term of this patent is extended or adjusted under 35 U.S.C. 154(b) by 0 days.

(21) Appl. No.: 17/273,035

(22) PCT Filed: Jul. 26, 2019

(86) PCT No.: PCT/RU2019/000525
§ 371 (c)(1),
(2) Date: Mar. 3, 2021

(87) PCT Pub. No.: WO2020/050742
PCT Pub. Date: Mar. 12, 2020

(65) Prior Publication Data
US 2021/0310011 A1    Oct. 7, 2021

(30) Foreign Application Priority Data
Sep. 4, 2018  (RU) .......................... RU2018131705

(51) Int. Cl.
*C12N 15/70* (2006.01)
*C12N 1/20* (2006.01)
*C12N 15/64* (2006.01)
*A61K 48/00* (2006.01)

(52) U.S. Cl.
CPC .............. *C12N 15/70* (2013.01); *C12N 1/20* (2013.01); *C12N 15/64* (2013.01); *A61K 48/00* (2013.01); *C12N 2800/90* (2013.01)

(58) Field of Classification Search
None
See application file for complete search history.

(56) References Cited

U.S. PATENT DOCUMENTS 6,573,100 B1    6/2003   Seeber et al.
2020/0385743 A1* 12/2020  Savelieva ............ C12N 15/70

OTHER PUBLICATIONS

Borja Gheorge M. et al. "Engineering *Escherichia coli* to increase plasmid DNA production in high cell-density cultivations in batch mode" Microbial Cell Factories 2012; 11(132): pp. 1-9, pp. 1-4.
Nierop Gijsbert P. et al. "Stimulation of homology-directed gene targeting at an endogenous human locus by a nicking endonuclease" Nucleic Acids Research, 2009; 37(17): pp. 5725-5736, abstract, DOI: 10.1093/nar/gkp643.

* cited by examiner

*Primary Examiner* — Suzanne M Noakes
(74) *Attorney, Agent, or Firm* — Nadya Reingand; Yan Hankin

(57) ABSTRACT

The invention can be used in biotechnology, in particular to the gene therapy DNA vector GDTT1.8NAS12, *Escherichia coli* strain JM 110-NAS, *Escherichia coli* strain JM 110-NAS/GDTT1.8NAS12, and the industrial production of the gene therapy DNA vector GDTT1.8NAS12. A method of obtaining the gene therapeutic DNA vector GDTT1.8NAS12 involves construction of a 2408-bp intermediate vector containing a 688-bp replication origin, a 467-bp transcription terminator hGH-TA, a 137-bp regulatory site RNA-out transposon TnIO, a I0I8-bp kanamycin resistance gene, and a 68-bp polylinker. Then, it is splitted using restriction endonucleases SalI and BamHI and ligated to the promoter regulatory region containing the 1219-bp promoter region of the human elongation factor EF1A with its own enhancer. The kanamycin resistance gene is cleaved at the SpeI restriction sites.

7 Claims, 6 Drawing Sheets
Specification includes a Sequence Listing.

pEGFP-C1        GDTT1.8NAS12

GENE THERAPY DNA VECTOR GDTT1.8NAS12 AND THE METHOD FOR OBTAINING THEREOF

FIELD OF THE INVENTION

The invention refers to genetic engineering and can be used in biotechnology, medicine, and agriculture for the manufacture of gene therapy products. I.e., the produced gene therapy DNA vector containing the therapeutic gene can be used to deliver it to the cells of human beings and animals that experience reduced or insufficient expression of that gene, thus ensuring the desired therapeutic effect.

REFERENCE TO A SEQUENCE LISTING

SEQ ID NO: 1 through SEQ ID NO: 37, incorporated fully by reference herein, are provided in ASCII format together in one separately enclosed .TXT file, submitted via EFS-Web—File name: SEQ-LISTING525-5-11-2021.txt; Date of Creation: Monday, May 17, 2021; File size: 16.0 KB.

BACKGROUND OF THE INVENTION

Gene therapy involves introduction of nucleic acids or their derivatives for treatment of acquired or hereditary diseases. The therapeutic effect is achieved either by compensation of malfunctioning or completely non-functional gene, or by production of a protein product with a therapeutic effect. The main tool of gene therapy is a therapeutic genetic material carrier, a vector. All vectors used in gene therapy are divided into two main categories, viral and non-viral ones. Viral gene therapy vectors are constructed on the basis of retroviruses, lentiviruses, adenoviruses, adeno-associated viruses, herpesviruses, poxviruses. (Lundstrom K. Viral Vectors in Gene Therapy. Diseases. 2018 May 21; 6(2)). Non-viral vectors include plasmid- or linear RNA-based vectors. Plasmid vectors have wider practical use due to simplified production and high stability. To enhance efficiency of therapeutic gene delivery to somatic cells, plasmid vectors are often introduced in combination with various carriers, such as lipids, cation polymers, dendrimers, polypeptides, and nanoparticles of different nature (Hidai C, Kitano H. Nonviral Gene Therapy for Cancer: A Review. Diseases. 2018 Jul. 3; 6(3)). A plasmid added to such molecular complex improves its penetration into cell.

Main advantage of viral vectors is fast and highly efficient delivery of therapeutic genetic material to a cell due to natural properties of viruses. However, the viral vectors have rather limited used in clinical practice. Besides purely technological issues related to obtainment, production and selection, viral vector application involves high risk of adverse medical consequences, such as inflammation and immune response to the gene therapy, cytotoxicity, mutagenesis, and carcinogenesis. Another risk of viral vectors is that specific individual features of patients can cause unpredictable consequences of gene therapy (Thomas C E, Ehrhardt A, Kay M A. Progress and problems with the use of viral vectors for gene therapy. Nat Rev Genet. 2003 May; 4(5):346-58). Despite intensive research aimed to reduce risks associated with gene therapy with viral vectors, many problems remain unsolved. In this regard, both researchers and clinicians grow ever more interested in application of non-viral vectors for therapeutic gene delivery.

A plasmid is a circle DNA molecule existing and replicating in a cell independently from the chromosome DNA. In vivo the plasmids occur mainly in bacteria and more rarely in archaea and eukaryotes. While chromosome DNA carries all genetic information required for life under normal conditions, plasmids are generally containing genes ensuring survival in specific or even adverse environment (Lipps G. (editor), (2008). Plasmids: Current Research and Future Trends. Caister Academic Press. ISBN 978-1-904455-35-6). Such genes ensure antibiotic resistance, encode virulence factors, take part in catabolism and metabolism of various substrates and detoxication of harmful compounds. Plasmids are known to participate in genetic information transfer between cells, thus enabling horizontal gene transfer.

Plasmid-based vectors do not share the downsides of viral vectors. Thus, plasmids are a convenient carrier for therapeutic genetic material by their nature, due to simple methods of direct molecular cloning and production of required amounts. Plasmid vector introduction does not cause inflammation and immune response of the subject. Plasmids themselves are not cytotoxic, and are not integrated into the genome when they reach target cells, and thus, they do not affect genome stability. Due to those features, plasmid vectors are a promising tool for gene therapy and genetic preventive therapy (DNA vaccines) (Porter K R, Raviprakash K. DNA Vaccine Delivery and Improved Immunogenicity. Curr Issues Mol Biol. 2017; 22:129-138).

Besides, quite extensive experience in operations with plasmid vectors is accumulated since they have been the main tool of molecular cloning and recombinant protein obtaining in scientific and biotechnological laboratories for decades. (Russel, David W.; Sambrook, Joseph (2001), Molecular cloning: a laboratory manual. Cold Spring Harbor, N.Y; Cold Spring Harbor Laboratory.)

However, the plasmid vectors have also some drawbacks limiting their use in the clinical practice. First, antibiotic resistance genes shall be introduced into plasmid vectors for selection and production in carrier strains. Second, regulatory elements (promoters, enhancers, posttranscriptional regulatory elements) are added to the vector for efficient expression of the therapeutic gene (Sun J, Li D, Hao Y, Zhang Y, Fan W, Fu J, Hu Y, Liu Y, Shao Y. Posttranscriptional regulatory elements enhance antigen expression and DNA vaccine efficiency. DNA Cell Biol. 2009 May; 28(5): 233-40) that mainly constitute viral nucleotide sequences (Draft Guideline on the quality, non-clinical and clinical aspects of gene therapy medicinal products ema.europa.eu/docs/en_GB/document_library/Scientific_quideline/2015/05/WC500187020.pdf. Finally, plasmid vector size determines efficiency of penetration into target cells, i.e. the bigger the vector, the poorer its penetration into cells is. Plasmids used in gene therapy often have unnecessary, non-encoding sites that increase their length substantially (Mairhofer J, Grabherr R. Rational vector design for efficient non-viral gene delivery: challenges facing the use of plasmid DNA. Mol Biotechnol. 2008.39(2):97-104).

The increase in antibiotic resistance of infectious agents over the past few years is a natural response to the wide-scale use of antimicrobial drugs in medicine. Increase in resistance to antibiotics is of great social and economic importance and is considered to be a threat to national security (MacPherson D. W., Gushulak B. D., Baine W. B., Bala S., Gubbins P. O., Holtom P., Segarra-Newnham M. 2009. Population mobility, globalization, and antimicrobial drug resistance. Emerg Infect Dis 15:1727-1732). In this regard, the use of plasmid vectors with antibiotic resistance genes added for selection and production bears a risk of transfer of such genes to infectious agents both directly and by horizontal transfer (San Millan A. Evolution of Plasmid- Mediated Antibiotic Resistance in the Clinical Context. Trends Microbiol. 2018 Jul. 23. doi: 10.1016/j.tim.2018.06.007). For that reason, the European Medicines Agency recommends refraining from adding antibiotic resistance genes to plasmid gene therapy vectors (Reflection paper on design modifications of gene therapy medicinal products during development/14 Dec. 2011 EMA/CAT/GTWP/44236/2009 Committee for advanced therapies).

The issue of necessary antibiotic resistance gene introduction into a plasmid vector can be avoided by developed *Escherichia coli* strains (DH1lacdapD and DH1lacP2dapD) featuring dapD gene in their genome controlled by lac promoter (Cranenburgh R M, Hanak J A, Williams S G, Sherratt D J. *Escherichia coli* strains that allow antibiotic-free plasmid selection and maintenance by repressor titration. Nucleic Acids Res. 2001. 29(5):E26). That gene encodes 2,3,4,5-tetrahydropyridine-2,6-dicarboxylate-N-succinyltransferase enzyme involved in biosynthesis of L-lysine. In the absence of inducer IPTG (isopropyl-β-D-1-thiogalactopyranoside) activating dapD expression, these strained are subject to lysis. Expression of dapD can also be induced by introduction of multicopy pORT vector, so that the transformed clones can be selected and multiplied. The disadvantage of these strains is a low transformation level and transformation instability.

Another way to avoid the use of antibiotic resistance genes involves modification of *Escherichia coli* cells so that RNA I plasmid vector replication inhibitor could suppress translation of genes critical to bacteria growth (such as murA encoding UDP-N-acetylglucosamine 1-carboxyvinyl-transferase enzyme involved in biosynthesis of bacterium cell wall peptidoglycan) by forming a duplex of RNA/antisense RNA (Mairhofer J, Pfaffenzeller I, Merz D, Grabherr R. A novel antibiotic free plasmid selection system: advances in safe and efficient DNA therapy. Biotechnol J. 2008. 3(1):83-89). The murA gene shall be controlled by tetR repressor protein and can be expressed only in the presence of constructed plasmid vector containing RNA-I gene. However, the inhibition mechanics is still unknown in this system, and IPTG-mediated induction results in development of *Escherichia coli* colonies devoid of the therapeutic plasmid vector.

Certain other ways to avoid application of antibiotic resistance genes in construction of plasmid gene therapy vectors have been described (Mignon C, Sodoyer R, Werle B. Antibiotic-free selection in biotherapeutics: now and forever. Pathogens. 2015 Apr. 3; 4(2):157-81).

In attempt to create a minimal vector without non-functional sequences, a supercoiled plasmid DNA molecule devoid of any prokaryotic nucleotide sequences has been obtained. This so-called minicircle vector only contained an origin of replication and antibiotic resistance gene and was obtained by integrase-mediated intramolecular recombination using φC31 phage (Chen Z Y, He C Y, Ehrhardt A, Kay M A. Minicircle DNA vectors devoid of bacterial DNA result in persistent and high-level transgene expression in vivo. Mol Ther. 2003. 8(3):495-500). However, such a gene is no viable for practical use due to extremely complex and labour-consuming industrial-scale obtainment and production processes.

Patent claim US 2011152377/10 proposed to use a plasmid vector devoid of antibiotic resistance genes that still encodes a repressor protein. This repressor protein suppresses expression of the toxic protein encoded in the chromosome DNA of *Escherichia coli*. However, the low efficiency and instability of such transformation limit production of vectors with repressor proteins on an industrial scale.

U.S. Pat. No. 7,521,182B2 suggests a plasmid vector containing araD gene. In *E. coli*, this gene encodes L-ribulose-5-phosphate-4-epimerase. Although this enzyme itself is not critical for bacterium growth, its deficiency results in toxic product accumulation in a cell. Vector encoding araD in combination with *E. coli* strain with this gene removed from the genome represents an antibiotic-free selection system.

U.S. Pat. No. 9,644,211 proposes a method of obtaining a minicircle plasmid vector free of prokaryotic sequences. Such a vector is produced by parA-mediated recombination realised in a cultured *E. coli* strain. Since this minicircle cannot be produced on an industrial scale, it cannot be viewed as a potential gene therapy vector.

The prototype for a new carrier based on recombinant plasmid gene therapy vectors was the recombinant vector for genetic vaccination (U.S. Pat. No. 9,550,998). The new carrier is a supercoiled plasmid that is used for the expression of cloned genes in human and animal cells. It consists of replication origin, promoter, and enhancer of human cytomegalovirus and regulatory elements from human T-lymphotropic virus.

The new vector is selected and produced in a special-purpose *Escherichia coli* strain by antisense-complementation of sacB gene introduced into the strain by a bacteriophage, thus excluding antibiotic resistance genes completely. The only factor limiting the use of the new vector in gene therapy is that it includes regulatory elements in the form of viral nucleotide sequences.

SUMMARY

The purpose of this invention is to construct a multipurpose gene therapy DNA vector for genetic modification of human and animal cells that would reasonably combine the following:

I) Efficiency of the gene therapy DNA vector in enhancing expression level of therapeutic genes in various human and animal tissue cells due to limited length not exceeding 2600 bp, ensuring efficient penetration into the target cell and availability of regulatory element sequences ensuring high expression of therapeutic genes in human and animal tissue cells.

II) Possibility of safe use in gene therapy of human beings and animals due to the absence of regulatory elements representing the nucleotide sequences of viral genomes in the gene therapy DNA vector.

III) Possibility of safe use in the gene therapy of human beings and animals due to the absence of antibiotic resistance genes in the gene therapy DNA vector.

IV) Producibility and constructability of gene therapy DNA vector on an industrial scale.

Item II and III are provided for herein in line with the recommendations of the state regulators for gene therapy medicines and, specifically, the requirement of the European Medicines Agency to refrain from adding antibiotic resistance marker genes to newly engineered plasmid vectors for gene therapy (Reflection paper on design modifications of gene therapy medicinal products during development/14 Dec. 2011 EMA/CAT/GTWP/44236/2009 Committee for advanced therapies) and refrain from adding viral genomes to newly engineered plasmid vectors for gene therapy (Guideline on the quality, non-clinical and clinical aspects of gene therapy medicinal products/23 Mar. 2015, EMA/CAT/80183/2014, Committee for Advanced Therapies).

The purpose of the invention also includes the construction of a strain carrying this gene therapy DNA vector for the production of these gene therapy DNA vectors on an industrial scale.

The specified purpose is achieved by creation of gene therapy DNA vector GDTT1.8NAS12 in the form of a 2591-bp circular double-strand DNA molecule containing nucleotide sequence SEQ ID No. 1, capable of autonomous replication in *Escherichia coli* cells and consisting of the following structural elements: promoter region of EF1A human elongation factor with its own enhancer contained in the first intron of the gene, a polylinker containing a sequence of BamHI, EcoRV, SalI, KpnI, EcoRI, XbaI, and NotI restriction sites and designed for cloning of therapeutic therapy genes, RNA-out regulatory element of transposon Tn10, enabling antibiotic-free positive selection for *Escherichia coli* strain JM 110-NAS; the origin of replication for autonomous replication of a gene therapy DNA vector with a single nucleotide substitution to increase plasmid production in the cells of most *Escherichia coli* strains.

Method of obtaining the 2591-bp gene therapy DNA vector GDTT1.8NAS12 involves initial construction of a 2408-bp intermediate vector containing a 688-bp replication origin, a 467-bp transcription terminator hGH-TA, a 137-bp regulatory site RNA-out of transposon Tn10, a 1018-bp kanamycin resistance gene, and a 68-bp polylinker, further vector splitting using SalI and BamHI restriction endonucleases and ligation with promoter/regulator site containing the promoter region of human elongation factor EFA with its own 1219-bp enhancer, and cleaving of the kanamycin resistance gene by SpeI restriction sites.

The method of obtaining of *Escherichia coli* strain JM110-NAS for the production of gene therapy DNA vector GDTT1.8NAS12 involves constructing a linear DNA fragment containing a 64-bp regulatory element RNA-in of Tn10 transposon allowing for antibiotic-free positive selection, 1422-bp sacB levansucrase gene, the product of which ensures selection within a sucrose-containing medium, 763-bp catR chloramphenicol resistance gene required to pick strain clones where homologous recombination occurred, and two homologous sequences, 329 bp and 233 bp, ensuring homologous recombination in the region of recA gene concurrent with gene inactivation, where the said homologous sequences are obtained by PCR amplification of recA gene fragment using genome DNA of *Escherichia coli* JM110-NAS as a matrix, and a couple of LHA-F (5'GCTGACGCTGCAGGTGATC, SEQ ID NO: 24) and LHA-R (5'-GACAAGATGTGTGTCTACCGCTTCAGGTTACCCGCCAG, SEQ ID NO: 25) primers, and a couple of RHA-F (5'-TGGCAGGGCGGGGCGTAACTACGCCTCTGTTCGTCTCGA SEQ ID NO: 26) and RHA-R (5'-CTCAGCAGCAACTCACGTAC, SEQ ID NO: 27) primers, and then the *Escherichia coli* cells are transformed by electroporation, and clones surviving in a medium containing 10 ug/ml of chloramphenicol are selected.

*Escherichia coli* strain JM110-NAS obtained by the method above for production of gene therapy DNA vector GDTT1.8NAS12 with possible antibiotic-free positive selection, containing a linear fragment consisting of regulator element RNA-in of transposon Tn10, sacB levansucrase gene, and catR chloramphenicol resistance gene in the chromosome in recA gene region.

The method of obtaining *Escherichia coli* strain JM110-AF/GDTT1.8NAS12 carrying gene therapy DNA vector GDTT1.8NAS12 involves making electrocompetent cells of *Escherichia coli* strain JM110-NAS and subjecting these cells to electroporation with gene therapy DNA vector GDTT1.8NAS12. After that, the cells are poured into agar plates (Petri dishes) with a selective medium containing yeastrel, peptone, 6% sucrose, and 10 μg/ml of chloramphenicol.

*Escherichia coli* strain JM110-NAS/GDTT1.8NAS12 obtained by the method described above, carrying gene therapy DNA vector GDTT1.8NAS12 for production of gene therapy DNA vector GDTT1.8NAS12 allowing for antibiotic-free selection.

The method of gene therapy DNA vector GDTT1.8NAS12 production on an industrial scale involves scaling-up the bacterial culture of *Escherichia coli* strain JM110-NAS/GDTT1.8NAS12 to the quantities necessary for increasing the bacterial biomass in an industrial fermenter, after which the biomass is used to extract a fraction containing the therapeutic DNA product, i.e. the gene therapy DNA vector GDTT1-8NAS12, and then multi-stage filtered, and purified by chromatographic methods.

BRIEF DESCRIPTION OF THE DRAWINGS

The essence of the invention is explained in the drawings, where

FIG. 1 marks the following structural elements of the vector:

(1) prom (695 to 1901 bp) is a promoter region of human elongation factor EF1A with an intrinsic enhancer contained in the first intron of the gene. It ensures efficient transcription of the recombinant gene in most human tissues.

(2) MCS (1902 to 1969 bp) is a polylinker (multiple cloning site) that contains a sequence of BamHI, EcoRV, SalI, KpnI, EcoRI, XbaI, and NotI restriction enzymes and allows cloning of the therapeutic therapy genes.

(3) RNA-out (2443 to 2579 bp out) is a regulatory element RNA-out of transposon Tn10 allowing for antibiotic-free positive selection in case of the use of *Escherichia coli* strain JM 110.

(4) on (1 to 688 bp) is an origin of replication for autonomous replication with a single nucleotide substitution to increase plasmid production in the cells of most *Escherichia coli* strains.

Figure 1:
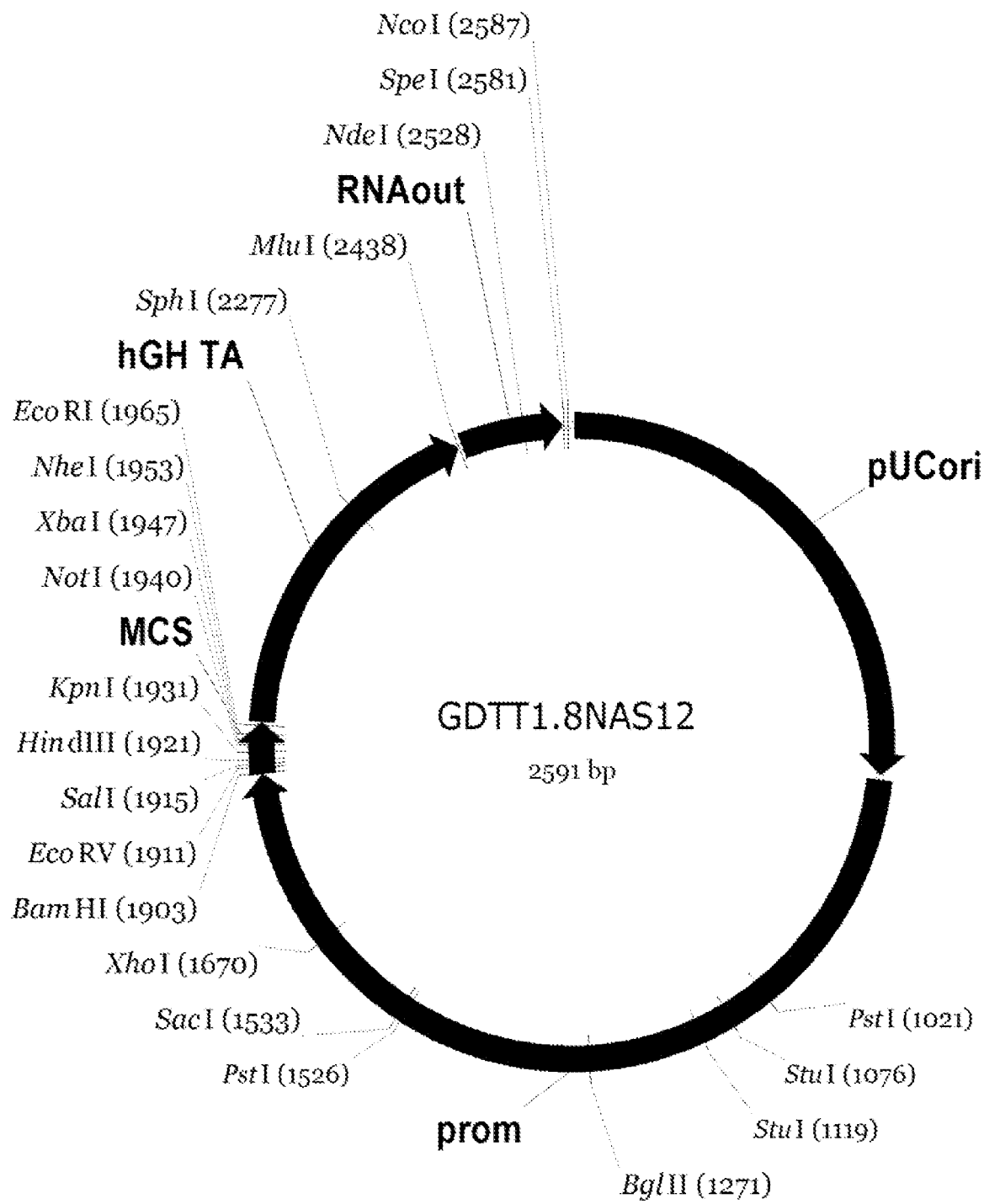
FIG. 1 shows the structure of gene therapy DNA vector GDTT1.8NAS12 that is a 2591-bp circular double-strand DNA molecule capable of autonomous replication in *Escherichia coli* cells.
Figure 2:
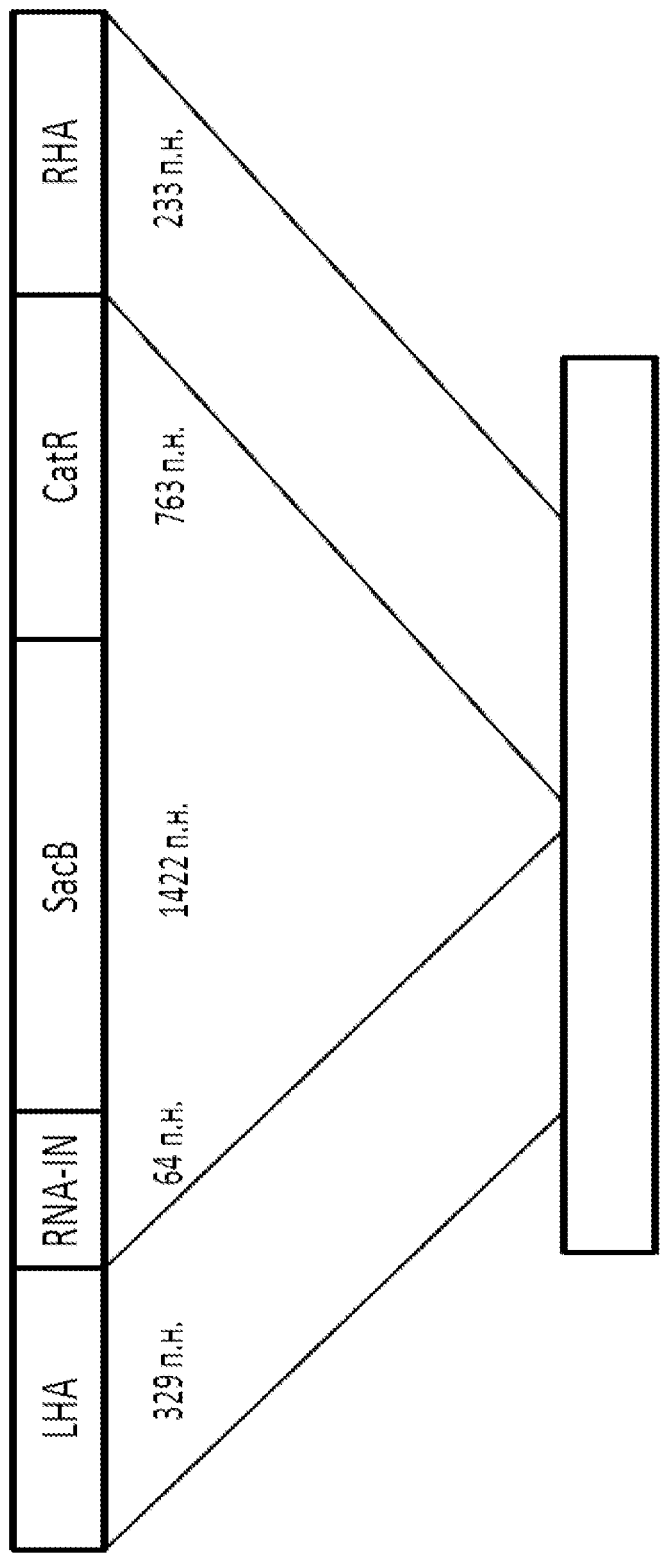

FIG. 2 shows the structure of the DNA fragment for homologous recombination in the region of recA gene of *Escherichia coli* for obtaining *Escherichia coli* strain JM 110.

The linear fragment consists of a cassette carrying the regulatory element RNA-IN of transposon Tn10 for antibiotic-free selection (64 bp), sacB levansucrase gene, the product of which ensures selection within a sucrose-containing medium (1422 bp), and catR chloramphenicol resistance gene required for the picking of strain clones in which homologous recombination occurred (763 bp). The cassette is flanked by two homology arms that ensure the process of recombination in the region of recA gene with concurrent gene inactivation (329 bp and 233 bp for the left arm and for the right arm, respectively).

Figure 3A:
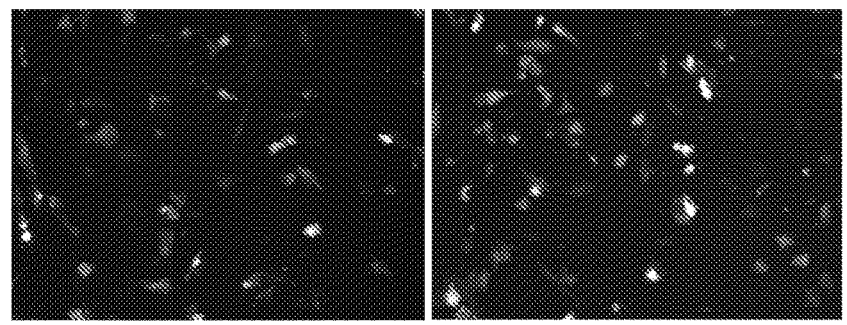
Figure 3B:
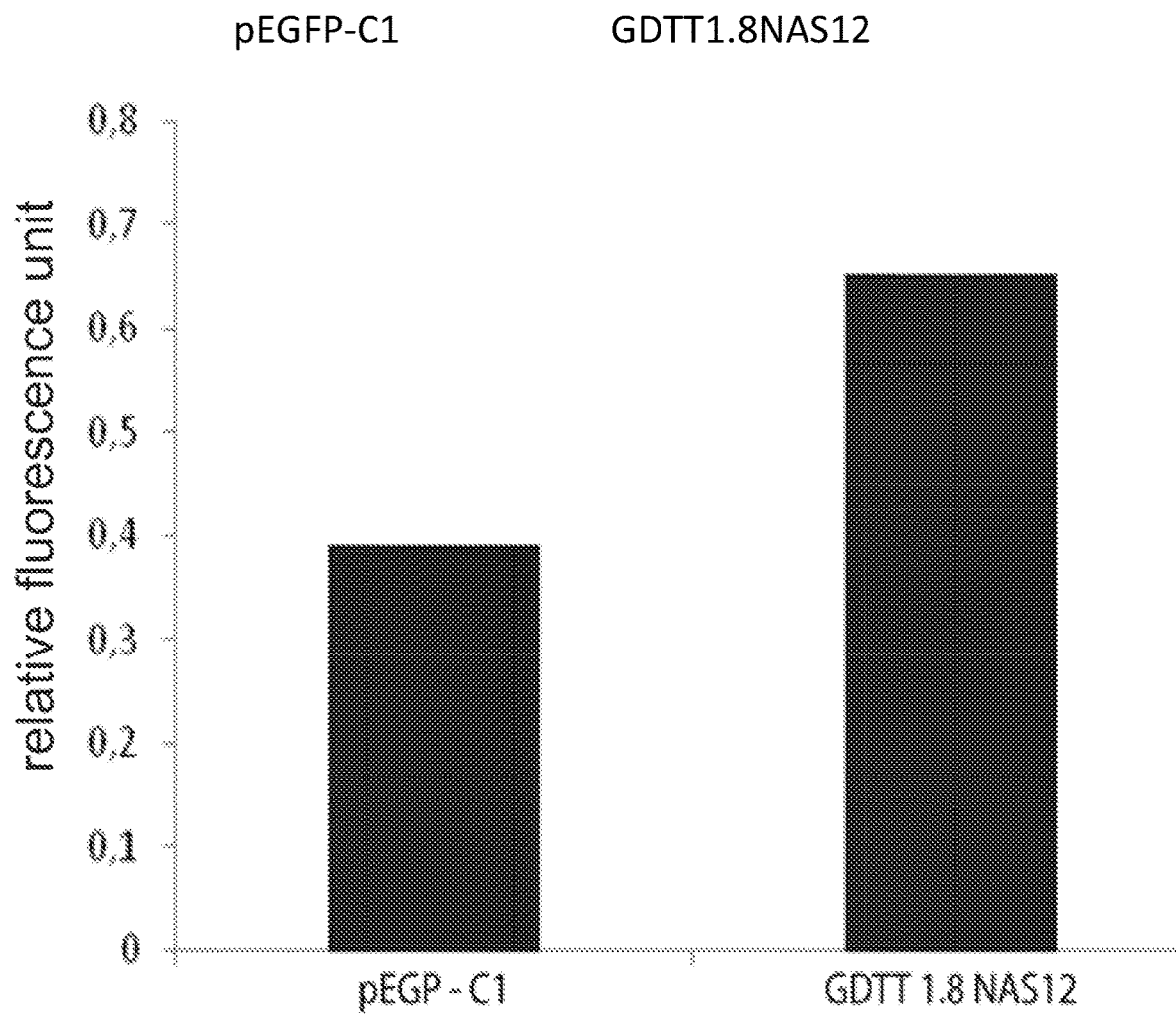

FIG. 3A-3B shows fluorescence microimaging of the MG-63 cell culture 48 hours after the transfection of the cells with pEFGP-C1 plasmid vector (Clontech) and DNA vector GDTT1.8NAS12-eGFP (FIG. 3A), and a diagram of fluorescence emitted by the protein extracted from MG-63 cells 48 hours after the transfection of the cells with pEFGP-C1 plasmid vector (Clontech) and DNA vector GDTT1.8NAS12-eGFP (FIG. 3B) to compare the levels of accumulation of the product of the target gene, e.g. green fluorescent protein (GFP), in the MG-63 cells 48 hours after the transfection of the cells with pEFGP-C1 plasmid vector (Clontech) and DNA vector GDTT1.8NAS12-eGFP.

Figure 4:
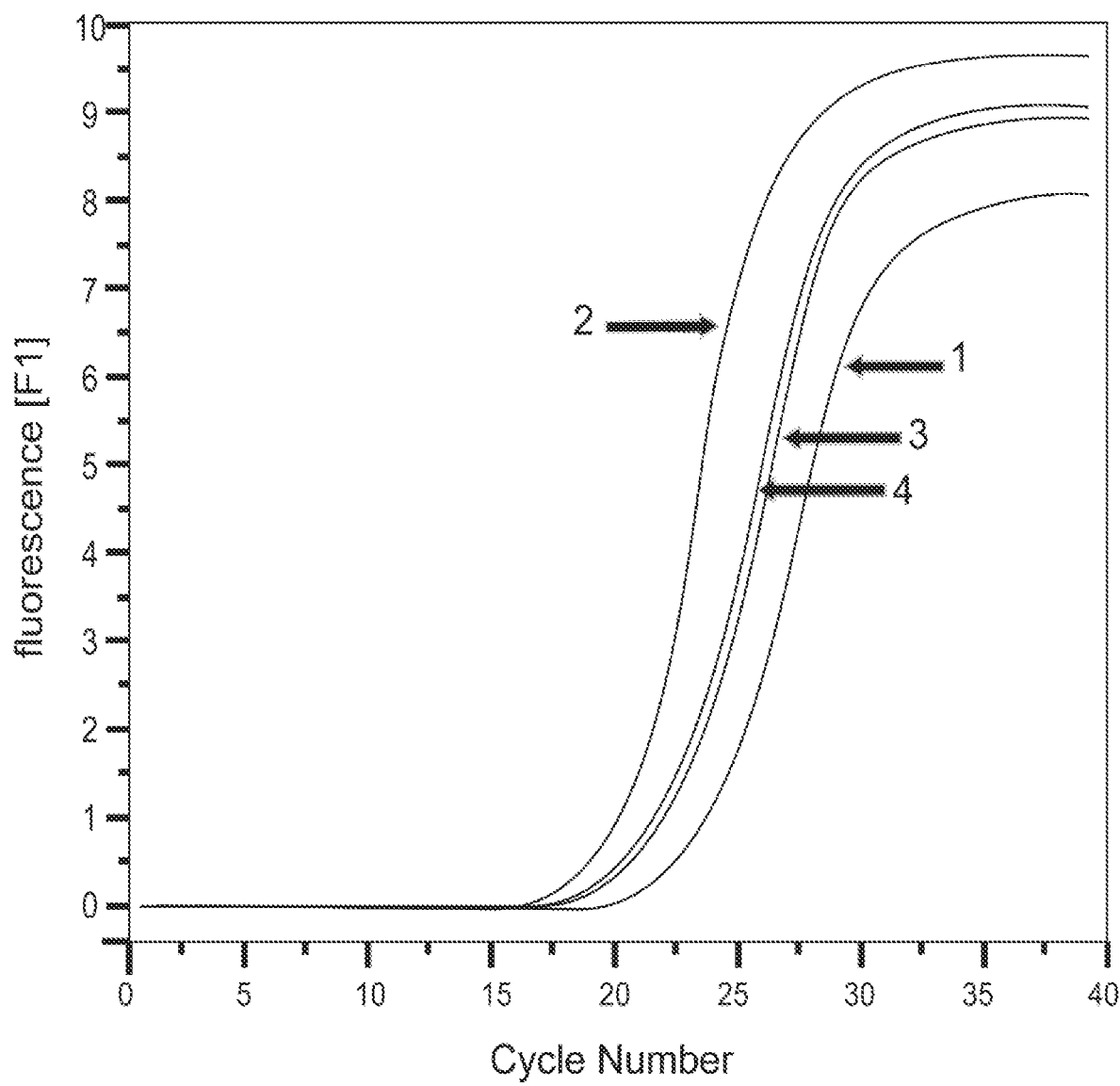

FIG. 4 shows diagrams of human glutathione peroxidase 1 gene mRNA accumulation in primary culture cells of epidermal keratinocytes HEKa before transfection and 48 hours after transfection of those cells with DNA vector GDTT1.8NAS12-GPX1 carrying a human glutathione peroxidase 1 gene, in order to assess therapeutic gene mRNA accumulation, e.g. for glutathione peroxidase 1 gene, in primary culture cells of HEKa epidermal keratinocytes before transfection and 48 hours after transfection of those cells with DNA vector GDTT1.8NAS12-GPX1 carrying a human glutathione peroxidase 1 gene, where:
1—cDNA of GPX1 gene after transfection with gene therapy vector GDTT1.8NAS12,
2—cDNA of GPX1 gene after transfection with gene therapy vector GDTT1.8NAS12-GPX1 carrying a region of human glutathione peroxidase 1 gene;
3—cDNA of B2M gene after transfection with gene therapy vector GDTT1.8NAS12,
4—cDNA of B2M gene after transfection with gene therapy vector GDTT1-8NAS12-GPX1 carrying a region of human glutathione peroxidase 1 gene.

Figure 5:
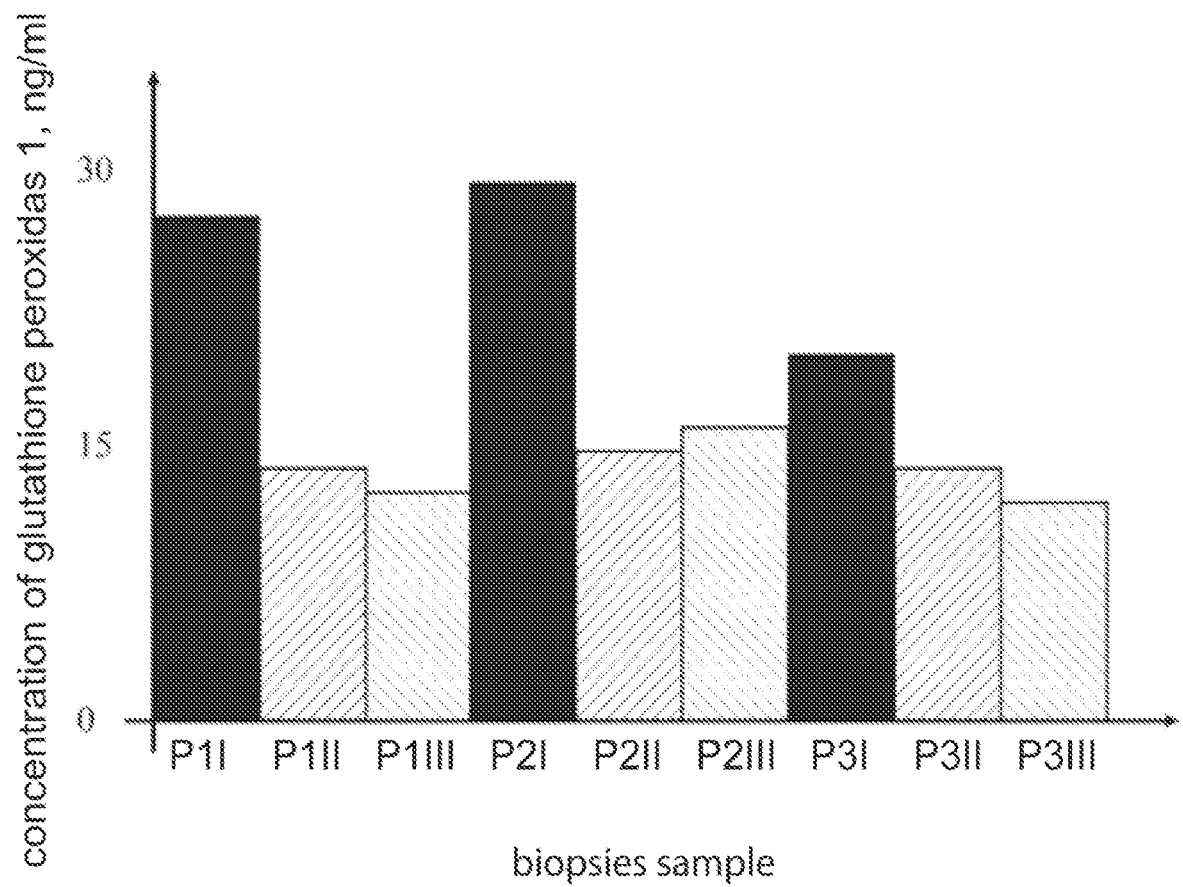

FIG. 5 shows the plot of glutathione peroxidase 1 protein concentration in skin biopsy samples of three patients after the injection of the skin of these patients with gene therapy DNA vector GDTT1.8NAS12-GPX1 carrying a human glutathione peroxidase 1 gene encoding region for the purpose of analysing changes in glutathione peroxidase 1 protein concentrations in human skin upon injection of human skin with gene therapy DNA vector GDTT1.8NAS12-GPX1 carrying the therapeutic gene, e.g. human glutathione peroxidase 1 gene, where:
P1I is patient P1 skin biopsy in the region of injection of gene therapy DNA vector GDTT1.8NAS12-GPX1,
P1II is patient P1 skin biopsy in the region of injection of gene therapy DNA vector GDTT1.8NAS12 (placebo),
P1III is patient P1 skin biopsy from intact site,
P2I is patient P2 skin biopsy in the region of injection of gene therapy DNA vector GDTT1.8NAS12-GPX1,
P2II is patient P2 skin biopsy in the region of injection of gene therapy DNA vector GDTT1.8NAS12 (placebo),
P2III is patient P2 skin biopsy from intact site,
P3I is patient P3 skin biopsy in the region of injection of gene therapy DNA vector GDTT1.8NAS12-GPX1,
P3II is patient P3 skin biopsy in the region of injection of gene therapy DNA vector GDTT1.8NAS12 (placebo),
P3III is patient P3 skin biopsy from intact site.

Figure 6:
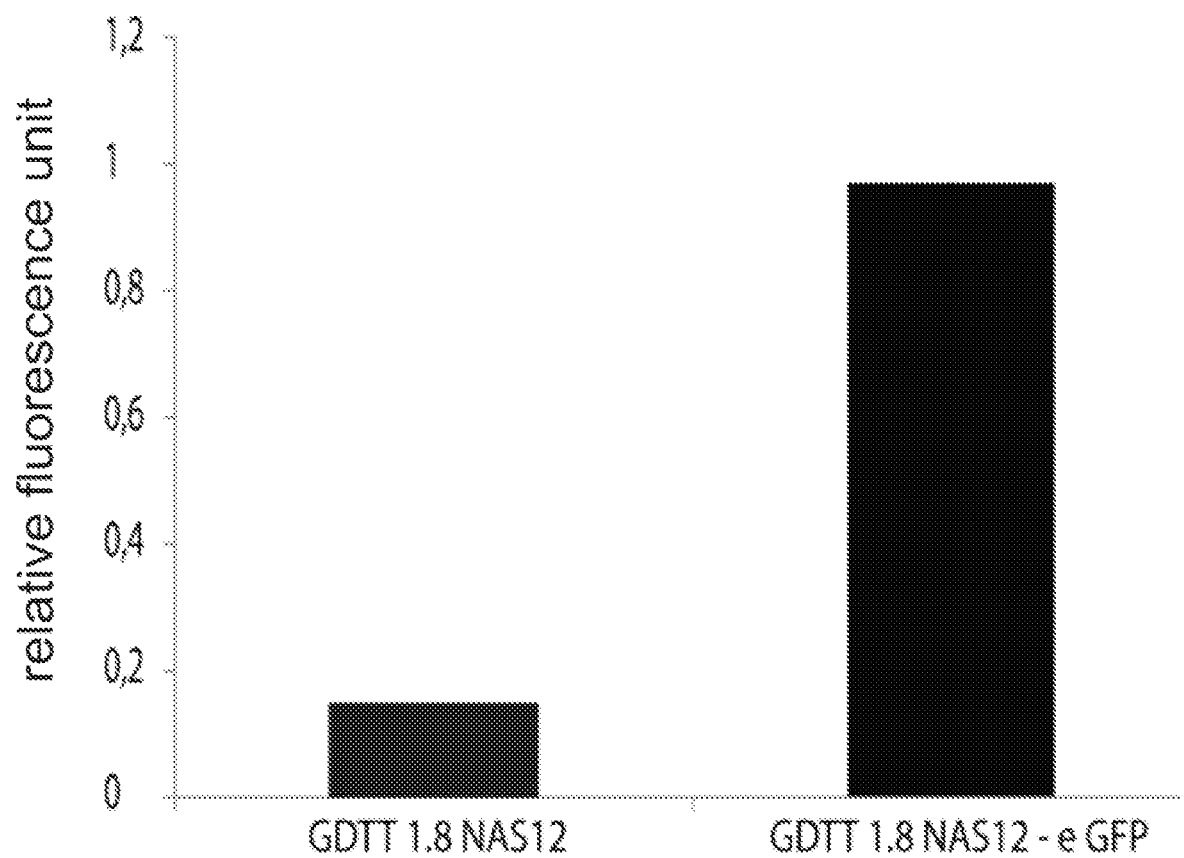

FIG. 6 shows a diagram of changes in fluorescence level of the green fluorescent protein in primary culture of BEnEpC bovine endometrial epithelial cells 48 hours after transfection with DNA vector GDTT1.8NAS12 and DNA vector GDTT1.8NAS12-eGFP carrying a gene site encoding green fluorescent protein, for comparison of the target gene product accumulation level, e.g. for the green fluorescent protein (GFP) in primary culture of BEnEpC bovine endometrial epithelial cells 48 hours after transfection with DNA vector GDTT1.8NAS12 and DNA vector GDTT1.8NAS12-eGFP carrying a gene site encoding green fluorescent protein.

EMBODIMENT OF THE INVENTION

The invention is embodied as follows.

First, a 2591-bp gene therapy DNA vector GDTT1.8NAS12 for genetic modification of animal and human cells containing nucleotide sequence SEQ ID No. 1 is constructed. Method of obtaining of the 2591-bp gene therapy DNA vector GDTT1.8NAS12 involves initial construction of a 2408-bp vector containing a 688-bp replication origin, a 467-bp transcription terminator hGH-TA, a 137-bp regulatory site RNA-out of transposon Tn10, a 1018-bp kanamycin resistance gene, and a 68-bp polylinker, further vector splitting using SalI and BamHI restriction endonucleases and ligation with promoter/regulator site containing the promoter region of EF1A human elongation factor with its own 1219-bp enhancer, and cleaving of the kanamycin resistance gene by SpeI restriction sites.

At the same time, degeneracy of genetic code is known to the experts in this field and means that the scope of this invention also includes variants of nucleotide sequences differing by insertion, deletion, or replacement of nucleotides that do not result in a change in the polypeptide sequence encoded by the therapeutic gene, and/or do not result in a loss of functional activity of the regulatory elements of GDTT1.8NAS12 vector and/or gene therapy DNA vectors carrying therapeutic genes based on it. Experts in this field realise that the methodological implementation of obtaining of gene therapy DNA vector GDTT1.8NAS12 and/or gene therapy DNA vectors carrying therapeutic genes based on it can vary within the choice of known methods of molecular gene cloning, and these methods are included in the scope of this invention. For example, different oligonucleotide sequences can be used to amplify genes, different restriction endonucleases or laboratory techniques, such as ligation independent cloning of genes.

To produce gene therapy DNA vector GDTT1.8NAS12 and/or gene therapy DNA vectors carrying therapeutic genes based on it with possible antibiotic-free positive selection, Escherichia coli strain JM110-NAS is constructed. The method of obtaining Escherichia coli strain JM110-NAS for production of gene therapy DNA vector GDTT1.8NAS12 and/or gene therapy DNA genes carrying therapeutic genes based on it involves construction of a linear DNA fragment containing a 64-bp regulatory element RNA-in of transposon Tn10 for antibiotic-free positive selection, a 1422-bp levansucrase gene sacB, the product of which ensures selection in sucrose-containing medium, a 763-bp chloramphenicol resistance gene catR required for selection of strain clones where homologous recombination occurred, and two homologous sequences, 329 bp and 233 bp, ensuring homologous recombination process in the region or recA gene with concurrent gene inactivation, and further transformation of Escherichia coli JM110 cells by electroporation, and selection of clones surviving in a medium containing 10 μg/ml of chloramphenicol. The method also involves construction of Escherichia coli strain JM110-NAS/GDTT1.8NAS12 carrying gene therapy DNA vector GDTT1.8NAS12 and/or gene therapy DNA vectors containing therapeutic genes based on it for vector production allowing for antibiotic-free selection. The method of obtaining Escherichia coli strain JM110-NAS/GDTT1.8NAS12 carrying gene therapy DNA vector GDTT1.8NAS12 and/or gene therapy DNA vectors containing therapeutic genes based on it involves obtainment of electrocompetent cells of Escherichia coli strain JM110-NAS and electroporation of those cells with gene therapy DNA vector GDTT1.8NAS12, with further inoculation in Petri dishes with selective agar medium containing yeastrel, peptone, 6% sucrose, and 10 μg/ml of chloramphenicol.

The method of gene therapy DNA vector GDTT1.8NAS12 production on an industrial scale involves scaling-up the bacterial culture of the strain to the quantities necessary for increasing the bacterial biomass in an industrial fermenter, after which the biomass is used to extract a fraction containing the therapeutic DNA product, i.e. the gene therapy DNA vector GDTT1-8NAS12, and then multistage filtered, and purified by chromatographic methods.

It is known to the experts in this field that culture conditions of producer strains, composition of nutrient media (except for antibiotic-free), equipment used, and DNA purification methods may vary within the framework of standard operating procedures depending on the particular production line, but known approaches to scaling, industrial production, and purification of DNA vectors using *Escherichia coli* strain JM110-NAS/GDTT1.8NAS12 fall within the scope of this invention.

The essence of the invention is explained in the following examples.

Example 1

Obtaining of gene therapy DNA vector GDTT1.8NAS12 containing a promoter of human elongation gene EF1a with its own enhancer for improved expression of therapeutic genes in cells of the most of human and animal cells.

Gene therapy DNA vector GDTT1.8NAS12 was constructed by consolidating six fragments of DNA derived from different sources:
(a) the origin of replication was produced by PCR amplification of a region of commercially available pUC19 plasmid with UCori-Bam and UCori-Nco oligonucleotides (List of Sequences, (1)-(2)),
(b) the hGH-TA transcription terminator was produced by PCR amplification of a site of human genomic DNA using hGH-F and hGH-R oligonucleotides (List of Sequences, (3) and (4)),
(c) the regulatory site RNA-OUT of transposon Tn10 was synthesised from RO—F, RO—R, RO-1, RO-2, and RO-3 oligonucleotides (List of Sequences, (5)-(9)),
(d) the kanamycin resistance gene was produced by PCR amplification of a site of commercially available pET-28 plasmid using Kan-F and Kan-R oligonucleotides (List of Sequences, (10) and (11)),
(e) the polylinker was produced by cining and annealing of four synthetic oligonucleotides MCS1, MCS2, MCS3, and MCS4 (List of Sequences, (12)-(15)),
(f) promoter/regulator site of human elongation factor gene EF1a with its own enhancer was obtained by PCR amplification of a human genome DNA site using EF1-Xho and EF1-R oligonucleotides (List of Sequences, (16)-(17)).

PCR amplification was performed using the commercially available kit Phusion® High-Fidelity DNA Polymerase (New England Biolabs) as per the manufacturer's instructions. The fragments (b), (c), and (d) had overlapping regions allowing for their consolidation with subsequent PCR amplification. Fragments (b), (c), and (d) were joined using hGH-F and Kan-R oligonucleotides (List of Sequences, (3) and (11)). Afterwards, the obtained DNA fragments were consolidated by restriction with subsequent ligation by BamHI and NcoI sites. This resulted in a vector still devoid of the polylinker. To introduce it, the plasmid was split by restriction endonucleases in BamHI and EcoRI sites with further ligation to the fragment (e). This resulted in a 2408-bp intermediate vector carrying a kanamycin resistance gene, but still without promoter/regulator site of elongation factor EF1a gene with its own enhancer. The vector obtained was split by restriction endonucleases in SalI and BamHI sites with further ligation to the fragment (f). This resulted in a 3608-bp vector carrying a kanamycin resistance gene and promoter/regulator site of elongation factor EF1a gene with its own enhancer. Then the kanamycin resistance gene was cleaved by SpeI restriction sites, and the remaining fragment was ligated to itself. Thus, a 2591-bp recombinant gene therapy DNA vector GDTT1.8NAS12 enabling antibiotic-free selection and expression of therapeutic genes cloned into it in the most types of human and animal tissues was obtained (SEQ ID No. 1).

Example 2

To prove the efficiency of DNA vector GDTT1.8NAS12, the therapeutic gene, e.g. the green fluorescent protein (GFP) gene, was cloned to the polylinker.

Obtaining of gene therapy DNA vector GDTT1.8NAS12-eGFP carrying the target gene, e.g. the gene coding green fluorescent protein (GFP).

The coding region of the green fluorescent protein gene was produced by PCR amplification of commercially available plasmid pEGFP-C1 (Clontech) using MVGFP-F and MVGFP-R oligonucleotides (List of Sequences, (18) and (19)). The obtained PCR fragment was cleaved by BamHI and EcoRI restriction endonucleases and ligated with a 3608-bp DNA vector carrying the kanamycin resistance gene and cleaved by the same enzymes. Further on, the kanamycin resistance gene was removed from the vector produced, as described in Example 1. This resulted in a 3268-bp DNA vector GDTT1.8NAS12-eGFP allowing for antibiotic-free selection.

Example 3

To prove the efficiency of DNA vector GDTT1.8NAS12, the therapeutic gene, e.g. the human glutathione peroxidase 1 (GPX1) gene, was cloned to a polylinker.

Obtaining of DNA vector GDTT1.8NAS12-GPX1 carrying a site of a therapeutic gene, such as GPX1 gene encoding human glutathione peroxidase 1 protein.

The 609-bp coding region of the GPX1 gene (SEQ ID No. 2) was produced by extracting total RNA from the patient's skin biopsy sample with subsequent reverse transcription and PCR amplification. The material was sampled from intact skin in the forearm, using the skin biopsy device Epitheasy 3.5 (Medax SRL). The patient's skin was preliminarily rinsed with sterile saline and anaesthetised with a lidocaine solution. Mass of the biopsy sample was about 10 mg. The sample was placed in 1 ml of Trizol Reagent (ThermoFisher Scientific), homogenised, and heated for 5 minutes at 65° C. The sample was centrifuged at 14,000 g for 10 minutes and heated again for 10 minutes at 65° C. Then 200 µl of chloroform was added, and the mixture was gently stirred and centrifuged at 14,000 g for 10 minutes. Then the water phase was isolated and mixed with 1/10 of the volume of 3M sodium acetate, pH 5.2, and an equal volume of isopropyl alcohol. The sample was incubated at −20° C. for 10 minutes and then centrifuged at 14,000 g for 10 minutes. The precipitated RNA was rinsed in 1 ml of 70% ethyl alcohol, air-dried and dissolved in 10 µl of RNase-free water. To synthesize the first strand of cDNA of the human glutathione peroxidase 1 gene, Mint reverse transcriptase (Evrogen, Russia) was used. 4 µl of Mint Buffer, 2 µl of dithiothreitol, 2 µl of dNTP Mix, 2 µl of each of oligonucleotides GPX1-F and GPX1-R (List of Sequences, (20) and (21)), and 2 µl of Mint reverse transcriptase were added to 6 μl of total RNA, and the mixture was incubated at 42° C. for 2 hours. The synthesised cDNA was used as a matrix in PCR amplification using the same oligonucleotides at 94° C. for 3 minutes; 30 cycles: at 94° C. for 30 seconds, at 60° C. for 30 seconds and at 72° C. for 45 seconds, with final elongation at 72° C. for 5 minutes. The obtained PCR fragment was cleaved by restriction endonucleases BamHI and EcoRI, and ligated with a 3608-bp vector carrying the kanamycin resistance gene and cleaved by the same enzymes. Further on, the kanamycin resistance gene was removed from the vector produced, as described in Example 1. This resulted in a 609-bp gene therapy DNA vector GDTT1.8NAS12-GPX1 carrying a region encoding the human glutathione peroxidase 1 gene allowing for antibiotic-free selection.

Example 4

Obtaining of *Escherichia coli* strain JM110-NAS for production of gene therapy DNA vector GDTT1.8NAS12 and/or gene therapy vectors carrying therapeutic genes based on it.

*Escherichia coli* strain JM110-NAS for the engineering of gene therapy DNA vector GDTT1.8NAS12 and/or gene therapy vectors carrying therapeutic genes based on it as produced by homologous recombination by introduction to its chromosome, specifically to the region of recA gene, of the linear fragment containing regulatory element RNA-in of transposon Tn10 allowing for antibiotic-free positive selection (64 bp), levansucrase gene sacB, the product of which ensures selection in a sucrose-containing medium (1422 bp), chloramphenicol resistance gene catR required for selection of strain clones in which homologous recombination occurred (763 bp), and two homologous sequences (homology arms) ensuring homologous recombination in the region of gene recA concurrent with gene inactivation (329 bp and 233 bp for the left arm and for the right arm, respectively).

To synthesise the left and the right homology arms, fragments of gene recA were amplified by PCR using the genomic DNA of *Escherichia coli* JM110 (Agilent Technologies, cat. No. 200239) as a matrix. To synthesise the left homology arm, LHA-F and LHA-R primers (List of Sequences, (22) and (23)) were used, while for synthesising the right homology arm, RHA-F and RHA-R primers (List of Sequences, (24) and (25)) were used. The RNA-IN fragment was tailed with IN—F, IN-1, IN-2, and IN-R synthetic oligonucleotides (List of Sequences, (26), (27), (28), (29)). The sacB gene was produced by PCR amplification using the genomic DNA of *B. subtilis* 168HT as a matrix, and SacB-F and SacB-R as primers (List of Sequences, (30) and (31)). To synthesise the catR gene, PCR amplification was performed using *Escherichia coli* BL21 pLysS as a matrix, and CatR-F and CatR-R (List of Sequences, (32) and (33)) as primers. PCR products LHA (the left homology arm), SacB, and RHA (the right homology arm) were amplified at 94° C. for 3 minutes; 30 cycles: at 94° C. for 20 seconds, at 60° C. for 20 seconds, and at 72° C. for 60 seconds, with final elongation at 72° C. for 5 minutes. PCR product RNA-IN was synthesized at 94° C. for 3 minutes; 30 cycles: at 94° C. for 10 seconds, at 60° C. for 10 seconds, and at 72° C. for 10 seconds, using oligonucleotides IN—F, IN-1, IN-2 and IN-R (List of Sequences, (26), (27), (28), and (29)) for the assembly of the fragment. For this, 10 μM of primers IN-F and IN-R, and 5 μM of primers IN-1 and IN-2 were used. PCR amplification was performed using the commercially available kit Phusion® High-Fidelity DNA Polymerase (Thermo Fisher Scientific) as per the manufacturer's instructions.

The linear fragment for homologous recombination was synthesised by consolidating five PCR products. All of the five products had overlapping areas allowing for subsequent assembly into a single fragment. All fragments were mixed in aliquots of 10 ng in a volume of 50 μl. The PCR product was derived at 94 C for 3 minutes; 10 cycles: at 94° C. for 30 seconds, at 60° C. for 30 seconds, and at 72° C. for 2 minutes, without primers added. Then LHA-F and RHA-R primers (List of Sequences, (22), (25)) were added, and 25 more PCR cycles were performed: at 94° C. for 30 seconds, at 60° C. for 30 seconds, and at 72° C. for 2 minutes, with final elongation at 72° C. for 5 minutes. This resulted in a 2811-bp long PCR fragment having the following structure: LHA-RNA-IN-SacB-CatR-RHA. This fragment was recovered preparatively from agarose gel using the DNA Elution Kit (BioSilica, Russia) according to the manufacturer's instructions.

For obtaining *Escherichia coli* strain JM110-NAS, electrocompetent cells were prepared. For this purpose, a single colony of *Escherichia coli* strain JM 110 (Agilent Technologies) was used to inoculate 10 ml of LB broth, and the cells were cultured overnight in an orbital shaker at 150 rpm and 37° C. On the following day, 1/20 was re-plated into 100 ml of LB broth and cultured in an orbital shaker at 150 rpm and 37° C. to reach $OD_{600}$=0.5. Upon reaching the required optical density, the cells were cooled down to 0° C. and centrifuged for 10 minutes at 4000 g. Then the medium was removed and the cells were rinsed with 100 ml of ice-cold bidistilled water twice to remove the remaining medium and then rinsed with 20 ml of 10% glycerine. After that, the cells were re-suspended in 1 ml of 10% glycerine and used for transformation.

Transformation with the obtained linear fragment was performed by electroporation in 1 mm cuvettes at 2 kV, 200 Ohm, 25 μF using the Gene Pulser Xcell (Bio-Rad, USA). The duration of the pulse was 4.9 ms to 5.1 ms. After that, the cells were cultivated in a SOC medium for 2.5 hours in an incubator shaker at 30° C. Then the cells were poured into LB agar plates (Petri dishes) containing 10 μg/ml of chloramphenicol. The cells were cultivated for 48 hours at 30° C. The picked-out clones were tested for survival in a selective medium containing yeastrel, peptone, 6% sucrose, and 10 μg/ml of chloramphenicol. The genotype of the resulting strain is recA rpsL (Strr) thr leu endA thi-1 lacY galK galT ara tonA tsx dam dcm supE44 Δ(lac-proAB) [F' traD36 proAB laclq ZΔM15]CmR sacB+.

Example 5

Obtaining of *Escherichia coli* strain JM110-NAS/GDTT1.8NAS12 carrying gene therapy DNA vector GDTT1.8NAS12 and/or gene therapy DNA vectors containing therapeutic genes based on it for production of the gene.

To prepare electrocompetent cells of *Escherichia coli* strain JM110-NAS, a single colony was used to infect 10 ml of LB broth, and the cells were cultured overnight in an orbital shaker at 150 rpm and 37° C. On the following day, 1/20 was re-plated into 100 ml of LB broth and cultured in an orbital shaker at 150 rpm and 37° C. to reach $OD_{600}$=0.5. Upon reaching the required optical density, the cells were cooled down to 0° C. and centrifuged for 10 minutes at 4000 g. Then the medium was removed and the cells were rinsed with 100 ml of ice-cold bidistilled water twice to remove the remaining medium and then rinsed with 20 ml of 10% glycerine. After that, the cells were re-suspended in 1 ml of 10% glycerine and used for transformation by electroporation. Electroporation was performed in 1 mm cuvettes at 2 kV, 200 Ohm, 25 µF using the Gene Pulser Xcell (Bio-Rad, USA). The duration of the pulse was 4.9 to 5.1 ms, and 1-10 ng of the vector was used. After that, the cells were cultivated in a SOC medium for 2.5 hours in an incubator shaker at 30° C. Then the cells were poured into agar plates (Petri dishes) with a selective medium containing yeastrel, peptone, 6% sucrose, and 10 µg/ml of chloramphenicol. Thus, *Escherichia coli* strain JM110-NAS/GDTT1.8NAS12 carrying gene therapy DNA vector GDTT1.8NAS12 was obtained. 48 hours later, a single colony was used to inoculate 10 ml of liquid selective medium containing yeastrel, peptone, 6% sucrose, and 10 µg/ml of chloramphenicol, and the medium was cultivated overnight in an orbital shaker at 150 rpm and 37° C. On the following day, the cells were pelleted, and DNA vector was extracted by alkaline lysis using GeneJET Plasmid Miniprep Kit (Thermo Fisher Scientific) according to the manufacturer's instructions.

*Escherichia coli* strain JM110-NAS/GDTT1.8NAS12 was deposited in the collection of the National Biological Resource Centre-Russian National Collection of Industrial Microorganisms (NBRC RNCIM, Russia) and NCIMB Patent Deposit Service (UK) (registration number VKPM-B-13234, date of deposit 21 Aug. 2018; INTERNATIONAL DEPOSITARY AUTHORITY No. NCIMB 43119, date of deposit 19 Jul. 2018).

Example 6

Proof of DNA Vector GDTT1.8NAS12 Efficiency.

To prove the efficiency of gene therapy DNA vector GDTT1.8NAS12, a target gene, e.g. the gene encoding green fluorescent protein (GFP), was cloned to a polylinker as per Example 2.

Comparison of levels of accumulation of a therapeutic gene, e.g. the green fluorescent protein (GFP), in human osteosarcoma cells MG-63 (ATCC CRL-1427) 48 hours after cell transfection with plasmid vector pEFGP-C1 (Clontech) and gene therapy DNA vector GDTT1.8NAS12-eGFP.

To evaluate the level of accumulation of the green fluorescent protein (GFP) in human osteosarcoma cells, the cells were transfected with plasmid vector pEFGP-C1 (Clontech) and gene therapy DNA vector GDTT1.8NAS12-eGFP was performed.

MG-63 cells were cultivated in the DMEM medium (Gibco) with 10% bovine embryo serum and 10 µg/ml gentamycin added. To achieve 90% confluence, the cells were seeded into a 24-well plate in the quantity of $4 \times 10^4$ cells per well in 24 hours before the transfection procedure. Lipofectamine 3000 (ThermoFisher Scientific, USA) was used as a transfection reagent. In test tube 1.1 µl of the solution of plasmid vector pEFGP-C1 and gene therapy DNA vector GDTT1.8NAS12-eGFP (500 ng/µl each) and 1 µl of reagent P3000 were added to 25 µl of Opti-MEM medium (Gibco). The preparation was mixed by gentle shaking. In the test tube 2, 1 µl of solution Lipofectamine 3000 was added to 25 µl of medium Opti-MEM (Gibco). The preparation was mixed by gentle shaking. The contents from test tube 1 were added to the contents of test tube 2, and the mixture was incubated at room temperature for 5 minutes. The resulting solution was added dropwise to the cells in the volume of 40 µl.

The results were recorded 48 hours later using the Olympus ix53 fluorescence microscope (Japan) with a 485/535 nm filter set (FIG. 3A). These results demonstrate that the transfection of HEK-293 cells with gene therapy DNA vector GDTT1.8NAS12-eGFP causes a significant increase in the accumulation of the green fluorescent protein as opposed with the transfection of the same cells with plasmid vector pEFGP-C1 (Clontech).

The results were recorded by measuring fluorescence of the protein extracted from the transfected cell line. For this purpose, the cells were rinsed from the well by pipetting and pelleted at 6000 rpm for 10 minutes, rinsed twice, and then the packed cells were re-suspended in 1 ml of sodium phosphate buffer. The cells were lysed in three freeze/thaw cycles at −70° C. Then the homogenate of lysed cells was pelleted at 13,000 g for 15 minutes. Supernatants were transferred into a 96-well culture plate (Grainer Bio-one) in four replicates for each sample, and then relative fluorescence of GFP was measured (absorption 455 nm/emission 538 nm) using Fluoroskan Ascent Microplate Fluorometer (Labsystems). The resulting values were normalised according to the total protein concentration in the sample that was measured by the Bradford protein assay. For this purpose, Coomassie Brilliant Blue R-250 (BioRad) was used as a dye. Each replicate was diluted in the wells of the 96-well plate (4 replicates for each sample) with water by a factor of 100, and then the dye was added. After that, optical density of all samples was measured at 620 nm using Multiskan Ascent (Thermo). The resulting values were compared with the calibration curve constructed for bovine serum albumin (Bio-Rad) with a series of sequential dilutions from 20 to 2.5 µg/ml. Calculations were made using the following formula:

$$\Sigma \text{amount of protein (µg)} = \{[x] - \sigma\} \div k \ast M,$$

where [x] is the mean value of $OD_{620}$ of the four replicates for each sample, σ is average deviation, k is the slope coefficient of the calibration curve for BSA, M is the dilution factor of the sample.

Based on the values of the total concentration of protein extracted from the cells, GFP fluorescence in the samples was normalized using the following formula:

$$OEn = [OE] \div \Sigma \text{amount of protein (mg)}$$

Where [OE] is the average of the four replicates for each sample, in relative fluorescence units.

The results are shown in FIG. 3B and demonstrate that the transfection of HEK-293 cells with gene therapy DNA vector GDTT1.8NAS12-eGFP increases the level of accumulation of the green fluorescent protein as opposed to the transfection of the same cells with plasmid vector pEFGP-C1 (Clontech).

Example 7

Proof of DNA Vector GDTT1.8NAS12 Efficiency.

To prove the efficiency of gene therapy DNA vector GDTT1.8NAS12, a therapeutic gene, e.g. the human glutathione peroxidase 1 (GPX1) gene, was cloned to a polylinker as per Example 3.

Changes in therapeutic gene mRNA accumulation, e.g. for glutathione peroxidase gene, in the primary culture cells of epidermal keratinocytes HEKa (PCS-200-011) 48 hours after transfection with the gene therapy DNA vector GDTT1.8NAS12-GPX1 carrying a human glutathione peroxidase 1 gene site.

Primary culture cells of epidermal keratinocytes HEKa were cultivated in the Dermal Cell Basal Medium (ATCC PCS-200-030) using Keratinocyte Growth Kit (ATCC PCS-200-040).

To achieve 90% confluence, 24 hours before the transfection procedure, the cells were seeded into a 24-well plate in the quantity of 5×10⁴ cells per well. Lipofectamine 3000 (ThermoFisher Scientific, USA) was used as a transfection reagent. The transfection with gene therapy DNA vector GDTT1.8NAS12-GPX1 carrying human glutathione peroxidase 1 gene was performed as described in Example 6. HEKa cells transfected with gene therapy DNA vector GDTT1.8NAS12 were used as a reference. Extraction of total RNA from the transfected cells and construction of the first cDNA strand was performed according to the procedure described in Example 3. To measure the level of mRNA expression in glutathione peroxidase 1 gene after transfection, real-time PCR (SYBR Green Real Time PCR) method was used. For the amplification of human GPX1-specific cDNA, GPX1-sf and GPX1-sR oligonucleotides were used (List of Sequences, (34), (35)). The length of amplification product is 241 bp. Beta-2 microglobulin (B2M) was used as a reference gene.

PCR amplification was performed using QuantiTect SYBR Green RT-PCR Kit (Qiagen, USA) or another real-time PCR kit in 20 μl of the amplification mixture containing: 25 μl of QuantiTect SYBR Green RT-PCR Master Mix, 2.5 mM of magnesium chloride, 0.5 μM of each primer, and 5 μl of total RNA. For the reaction, CFX96 amplifier (Bio-Rad, USA) was used under the following conditions: 1 cycle of reverse transcription at 42° C. for 30 minutes, denaturation at 98° C. for 15 minutes followed by 40 cycles comprising denaturation at 94° C. for 15 s, annealing of primers at 60° C. for 30 s and elongation at 72° C. for 30 s. Positive control included amplicons from PCR on matrices represented by plasmids in known concentrations containing cDNA sequences of human glutathione peroxidase 1 and B2M genes. Negative control included deionised water. Real-time quantification of the PCR products, i.e. GPX-1 and B2M gene cDNA obtained by amplification, was conducted using the Bio-Rad CFX Manager 2.1 software.

To confirm increased expression of glutathione peroxidase 1 gene in the primary culture cells of epidermal keratinocytes HEKa after transfection with the gene therapy DNA vector GDTT1.8NAS12-GPX1 carrying a human glutathione peroxidase 1 gene site, the FIG. 4 shows PCR product accumulation diagrams.

The figure shows that transfection with gene therapy DNA vector GDTT1.8NAS12-GPX1 carrying a therapeutic gene, e.g. the human glutathione peroxidase 1 gene, causes the level of human glutathione peroxidase 1 gene-specific cDNA to rise massively.

Example 8

Proof of DNA Vector GDTT1.8NAS12 Efficiency.

To prove the efficiency of gene therapy DNA vector GDTT1.8NAS12, a therapeutic gene, e.g. the glutathione peroxidase 1 gene, was cloned to a polylinker as per Example 3.

Measurements were made of the changes in the concentration of the glutathione peroxidase 1 protein in human skin upon injection of gene therapy DNA vector GDTT1.8NAS12-GPX1 carrying a therapeutic gene, e.g. the human glutathione peroxidase 1 gene, into human skin.

To analyse changes in the concentration of the glutathione peroxidase 1 protein, gene therapy DNA vector GDTT1.8NAS12-GPX1 carrying a region encoding the glutathione peroxidase 1 gene was injected into the forearm skin of three patients, with concurrent introduction of a placebo being gene therapy DNA vector GDTT1.8NAS12 without the glutathione peroxidase 1 gene cDNA. Patient 1, woman, 66 y.o. (P1); Patient 2, woman, 65 y.o. (P2); Patient 3, man, 59 y.o. (P3).

Gene therapy DNA vector GDTT1.8NAS12 (placebo) and gene therapy DNA vector GDTT1.8NAS12-GPX1 carrying a region of glutathione peroxidase 1 gene were injected in the quantity of 1 mg for each genetic construct by the tunnel method with a 30G needle to the depth of 3 mm. The injected volume of gene therapy DNA vector GDTT1.8NAS12 (placebo) and gene therapy DNA vector GDTT1.8NAS12-GPX1 carrying a region of glutathione peroxidase 1 gene was 1-0.3 ml for each genetic construct. The points of introduction of each of the genetic constructs were located at 8-10 cm from each other.

The biopsy samples were taken on the 2nd day after the injection of the gene therapy DNA vectors. The biopsy samples were taken from the patients' skin in the area of the introduction of gene therapy DNA vector GDTT1.8NAS12-GPX1 carrying a region encoding the glutathione peroxidase 1 gene (I), gene therapy DNA vector GDTT1.8NAS12 (placebo) (II), and from intact skin (III), using the skin biopsy device Epitheasy 3.5 (Medax SRL). The skin of the patients was preliminarily rinsed with sterile saline and anaesthetised with a lidocaine solution. The biopsy sample volume was ca. 10 mm3, and the weight was ca. 15 mg. The sample was placed in a buffer solution containing 50 mM of Tris-HCl, pH 7.6, 100 mM of NaCl, 1 mM of EDTA, and 1 mM of phenylmethylsulfonyl fluoride and homogenised to obtain a homogenised suspension. The resulting suspension was then centrifuged for 10 minutes at 14,000 g. Supernatant was collected and used to assay the therapeutic protein by enzyme-linked immunosorbent assay (ELISA) using the ELISA Kit for Glutathione Peroxidase 1 (GPX1) (Cloud-Clone Corp., USA) according to the manufacturer's method with optical density detection using ChemWell Automated EIA and Chemistry Analyser (Awareness Technology Inc., USA).

Concentration was quantified by a calibration curve plotted using the reference samples from the kit with known concentrations of glutathione peroxidase 1 protein was used. The method sensitivity is 5.2 ng/ml, measurement range is 12.5-200 ng/ml. Diagrams resulting from the assay are shown in FIG. 5. The skin of each of the three patients demonstrates an increased concentration of the glutathione peroxidase 1 protein in the area of introduction of gene therapy DNA vector GDTT1.8NAS12 carrying a therapeutic gene, e.g. the human glutathione peroxidase 1 gene, compared to the concentration of the glutathione peroxidase 1 protein in the area of introduction of gene therapy DNA vector GDTT1.8NAS12 (placebo) devoid of the region of the human glutathione peroxidase 1 gene.

Example 9

Proof of DNA Vector GDTT1.8NAS12 Efficiency.

To prove the efficiency of gene therapy DNA vector GDTT1.8NAS12, a target gene, e.g. the gene encoding green fluorescent protein (GFP), was cloned to a polylinker as per Example 2.

The levels of accumulation of a target gene, e.g. the green fluorescent protein (GFP), in primary culture cells of bovine endometrial epithelium (BEnEpC, CellApplications, Inc.) in 48 hours after cell transfection with gene therapy DNA vector GDTT1.8NAS12-eGFP were compared.

To quantify the level of accumulation of the green fluorescent protein (GFP) in primary culture cells of bovine endometrial epithelium, the cells were transfected with gene therapy DNA vector GDTT1.8NAS12-eGFP.

The cells were cultivated with the use of Bovine Endometrial Cell Growth Media Kit (CellApplications, Inc.) as per manufacturer's instructions. To achieve 90% confluence, 24 hours before the transfection procedure, the cells were seeded into a 24-well plate in the quantity of $3 \times 10^4$ cells per well. Lipofectamine 3000 (ThermoFisher Scientific, USA) was used as a transfection reagent. Transfection was performed according to the procedure described in Example 6. Gene therapy DNA vector GDTT1.8NAS12 free of the green fluorescent protein gene was used as a reference. The results were recorded by measuring fluorescence of the protein extracted from the transfected cell line, as described in Example 6.

The results are shown in FIG. 6 and allow us to conclude that the transfection of the primary cell line of bovine endometrial epithelium with gene therapy DNA vector GDTT1.8NAS12-eGFP carrying the green fluorescent protein gene leads to a higher level of accumulation of the green fluorescent protein comparing with the transfection of the same cells with gene therapy vector GDTT1.8NAS12 devoid of the green fluorescent protein gene.

Example 10

To confirm the producibility and constructability of gene therapy DNA vector GDTT1.8NAS12 and/or gene therapy DNA vectors carrying therapeutic genes based on it, a large-scale fermentation of *Escherichia coli* strain JM110-NAS/GDTT1.8NAS12 was performed.

Fermentation of *Escherichia coli* strain JM110-NAS/GDTT1.8NAS12 carrying gene therapy DNA vector GDTT1.8NAS12 was performed in a 10l fermenter with subsequent extraction of gene therapy DNA vector GDTT1.8NAS12.

For the fermentation of *Escherichia coli* strain JM110-NAS/GDTT1.8NAS12, a medium was prepared containing per 10 l: 100 g of tryptone, 50 g of yeastrel (Becton Dickinson), then the medium was diluted with water to 8,800 ml and autoclaved at 121° C. for 20 minutes, and then 1,200 ml of 50% (w/v) sucrose was added. After that, the seed culture of *Escherichia coli* strain JM110-NAS/GDTT1.8NAS12 was inoculated into a culture flask in the volume of 100 ml. The culture was incubated in an incubator shaker for 16 hours at 30° C. The seed culture was transferred to the Techfors S bioreactor (Infors HT, Switzerland) and grown to a stationary phase. The process was controlled by measuring optical density of the culture at 600 nm. The cells were pelleted for 30 minutes at 5,000-10,000 g. Supernatant was removed, and the cell pellet was re-suspended in 10 vol % phosphate buffered saline. The cells were centrifuged again for 30 minutes at 5,000-10,000 g. Supernatant was removed, a solution of 20 mM TrisCl, 1 mM EDTA, 200 g/l sucrose, pH 8.0, was added to the cell pellet in the volume of 1,000 ml, and the mixture was stirred thoroughly to a homogenised suspension. Then egg lysozyme solution was added to the final concentration of 100 µg/ml. The mixture was incubated for 20 minutes on ice while stirring gently. Then 2,500 ml of 0.2M NaOH, 10 g/l sodium dodecyl sulphate (SDS) was added, the mixture was incubated for 10 minutes on ice while stirring gently, then 3,500 ml of 3M sodium acetate, 2M acetic acid, pH 5-5.5 was added, and the mixture was incubated for 10 minutes on ice while stirring gently. The resulting sample was centrifuged for 20-30 minutes at 15,000 g or a greater value. The solution was decanted delicately, and residual precipitate was removed by passing through a coarse filter (filter paper). Then RNase A (Sigma) was added to the final concentration of 20 µg/ml, and the solution was incubated overnight for 16 hours at room temperature. The solution was then centrifuged for 20-30 minutes at 15,000 g and passed through a 0.45 µm membrane filter (Millipore). Then ultrafiltration was performed with a membrane of 100 kDa (Millipore) and the mixture was diluted to the initial volume with a buffer solution of 25 mM TrisCl, pH 7.0. This manipulation was performed three to four times. The solution was applied to the column with 250 ml of DEAE Sepharose HP (GE, USA), equilibrated with 25 mM TrisCl, pH 7.0. After the application of the sample, the column was washed with three volumes of the same solution, and then gene therapy DNA vector GDTT1-8NAS12 was eluted using a linear gradient of 25 mM Tris-HCl, pH 7.0, to obtain a solution of 25 mM Tris-HCl, pH 7.0, 1M NaCl, five times the volume of the column. The elution process was controlled by measuring optical density of the run-off solution at 260 nm. Chromatographic fractions containing gene therapy DNA vector GDTT1.8NAS12 were joined together and subjected to gel filtration by Superdex 200 sorbent (GE, USA). The column was equilibrated with phosphate buffered saline. The elution process was controlled by measuring optical density of the run-off solution at 260 nm, and the fractions were analysed by agarose gel electrophoresis. Fractions containing gene therapy DNA vector GDTT1.8NAS12 were joined and stored at −20° C. These process operations were repeated three times to evaluate the process reproducibility. The process reproducibility and quantitative characteristics of final product yield confirm the producibility and constructability of gene therapy DNA vector GDTT1.8NAS12, and/or gene therapy DNA vectors carrying therapeutic genes based on it, on an industrial scale.

Therefore, the purpose of this invention, specifically the construction of a multipurpose gene therapy DNA vector for genetic modification of human and animal cells that would reasonably combine:

1) Efficiency of the gene therapy DNA vector in enhancing expression level of therapeutic genes in various human and animal tissue cells due to limited length not exceeding 2600 bp, namely 2591 bp, ensuring efficient penetration into a target cell and availability of regulatory element sequences ensuring high expression of therapeutic genes in the most human and animal tissue cells.

II) Possibility of safe use in gene therapy of human beings and animals due to the absence of regulatory elements representing the nucleotide sequences of viral genomes in the gene therapy DNA vector.

III) Possibility of safe use in the gene therapy of human beings and animals due to the absence of antibiotic resistance genes in the gene therapy DNA vector.

IV) Producibility and constructability of gene therapy DNA vector and/or gene therapy DNA vectors carrying therapeutic genes based on it, on an industrial scale has been achieved, which is supported by the following examples: 1, 6, 7, 8, 9 for Item (I); Example 1 for Item (II); Example 1 for Item (III); Examples 4, 5, 10 for Item (IV).

INDUSTRIAL APPLICABILITY

All examples listed above prove industrial applicability of the proposed gene therapy DNA vector GDTT1.8NAS12, method for obtaining thereof, *Escherichia coli* strain JM110-NAS for production of DNA vector GDTT1.8NAS12, method of obtaining of *Escherichia coli* strain JM110-NAS, *Escherichia coli* strain JM110-NAS/GDTT1.8NAS12 including gene therapy DNA vector GDTT1.8NAS12 for their production, method of obtaining of *Escherichia coli* strain JM110-NAS/GDTT1.8NAS12, and method of industrial-scale production of the gene therapy DNA vector.

LIST OF ABBREVIATIONS

GDTT1.8NAS12 is a gene therapy vector devoid of sequences of viral genomes and antibiotic resistance markers
- DNA—Deoxyribonucleic acid
- cDNA—Complementary deoxyribonucleic acid
- RNA—Ribonucleic acid
- mRNA—Messenger ribonucleic acid
- bp—base pair
- PCR—Polymerase chain reaction
- ml—millilitre, μl—microliter
- l—litre
- μg—microgram
- mg—milligram
- g—gram
- μM—micromol
- mM—millimol
- min—minute
- s—second
- rpm—rotations per minute
- nm—nanometre
- cm—centimetre
- mW—milliwatt
- RFU—Relative fluorescence unit
- PBS—Phosphate buffered saline

What is claimed is:

1. A gene therapy DNA vector GDTT1.8NAS12 comprising a 2591-bp circular double-stranded DNA molecule comprising nucleotide sequence SEQ ID NO: 1, wherein said GDTT1.8NAS12 vector is capable of autonomous replication in Escherichia coli cells and consisting of following structural elements: a promoter region of EF1A human elongation factor with its own enhancer located in a first intron of the gene, a polylinker comprising restriction site sequences BamHI, EcoRV, SalI, KonI, EcoRI, XbaI, and NotI restriction sites designed for cloning of therapeutic genes, an RNA-out regulatory element transposon Tn10 which enables antibiotic-free positive selection for Escherichia coli strain JM110-NAS; an origin of replication for the autonomous replication of a gene therapy DNA vector which further consists of a single nucleotide substitution that increases plasmid production in Escherichia coli strains compared to Escherichia coli strains not having said substitution.

2. A method of making the gene therapy DNA vector GDTT1.8NAS12 according to claim 1 comprising, initial construction of an intermediate vector comprising a 688-bp replication origin, a 467-bp transcription terminator NGH-TA, a 137-bp regulatory site RNA-out of transposon Tn10, a 1018-bp kanamycin resistance gene, and a 68-bp polylinker to make the intermediate vector, and further splitting the vector by contacting with SalI and BamHI restriction endonucleases followed by and ligation with a promoter/regulator site comprising the promoter region of human elongation factor EF1A with its own 1219-bp enhancer, and cleaving of the kanamycin resistance gene by SpeI restriction sites to make the gene therapy DNA vector GDTT1.8NAS12.

3. A method of making Escherichia coli strain JM110-NAS into a strain for the production of gene therapy DNA vector GDTT1.8NAS123 according to claim 1 comprising constructing a linear DNA fragment containing a regulatory element RNA-in of Tn10 transposon allowing for antibiotic-free positive selection (64 bp), a levansucrase gene sacB which ensures selection within a sucrose containing medium (1422 bp), a chloramphenicol resistance gene catR which is required to pick strain clones where homologous recombination occurs (763 bp), and two homologous sequences (329 bp and 233 bp) that induce homologous recombination in the region of the recA gene which also induces gene inactivation of said recA, wherein said homologous sequences are obtained by PCR amplification of a recA gene fragment comprising genome DNA of Escherichia coli JM110-NAS as a matrix, and wherein LHA-F (5'-GCTGACGCTGCAGGTGATC, SEQ ID NO:24) and LHA-R (5'-GACAAGATGTGTGTCTACCGCTTCAGGT-TACCCGCCAG, SEQ ID NO: 25) primers, and RHA-F (5'-TGGCAGGGCGGGGCGTAAC-TACGCCTCTGTTCGTCTCGA, SEQ ID NO: 26) and RHA-R(5'-CTCAGCAGCAACTCACGTAC, SEQ ID NO: 27) primers are utilized for said homologous recombination, and transforming Escherichia coli JM110-NA cells by electroporation, and selecting clones surviving in a medium containing 10 ug/mi of chloramphenicol.

4. Escherichia coli strain JM110-NAS comprising the gene therapy vector according to claim 1 and obtained via the method described in claim 3 for production of gene therapy DNA vector GDTT1.8NAS12 that allows antibiotic-free positive selection, having a linear fragment consisting of regulatory element RNA-in of transposon Tn10, levansucrase gene sacB, and the chloramphenicol resistance gene catR homologously recombined in the chromosome in the recA gene region.

5. The A method of obtaining Escherichia coli strain JM110-NAS/GDTT1.8NAS12 comprising the gene therapy DNA vector GDTT1.8NAS12 according to claim 1, comprising making electrocompetent cells of Escherichia coli strain JM 110-NAS according to claim 3 and subjecting these cells to electroporation with the gene therapy DNA vector GDTT1.8NAS12 according to claim 1, and further comprising adding the cells onto agar plates with a selective medium comprising yeastrel, peptone, 6% sucrose, and 10 μg/ml of chloramphenicol and growing said Escherichia coli cells on said agar plates.

6. The Escherichia coli strain JM110-NAS/GDTT1.8NAS12 grown according to claim 5, wherein said strain is selected by antibiotic-free selection.

7. A method of producing the gene therapy DNA vector according to claim 1 on an industrial scale, comprising scaling-up a bacterial culture of the strain according to claim 6 to quantities necessary for increasing a bacterial biomass in an industrial fermenter, and extracting from the biomass a fraction containing the therapeutic gene therapy DNA vector GDTT1.8NAS12, followed by multi-stage filtration, and purification by chromatographic methods.

* * * * *

SEQUENCE LISTING

```
<160> NUMBER OF SEQ ID NOS: 37

<210> SEQ ID NO 1
<211> LENGTH: 2591
<212> TYPE: DNA
<213> ORGANISM: Homo Sapiens

<400> SEQUENCE: 1
ataacgcagg aaagaacatg tgagcaaaag gccagcaaaa ggccagggac cgtaaaaagg      60
ccgcgttgct ggcgtttttc cataggctcc gcccccctga cgagcatcac aaaaatcgac     120
gctcaagtca gaggtggcga acccgacag gactataaag ataccaggcg tttccccctg     180
gaagctccct cgtgcgctct cctgttccga ccctgccgct taccggatac ctgtccgcct     240
ttctcccttc gggaagcgtg gcgctttctc atagctcacg ctgtaggtat ctcagttcgg     300
tgtaggtcgt tcgctccaag ctgggctgtg tgcacgaacc ccccgttcag cccgaccgct     360
gcgccttatc cggtaactat cgtcttgagt ccaacccggt aagacacgac ttatcgccac     420
tggcagcagc cactggtaac aggattagca gagcgaggta tgtaggcggt gctacagagt     480
tcttgaagtg gtggcctaac tacggctaca ctagaagaac agtatttggt atctgcgctc     540
tgctgaagcc agttaccttc ggaaaaagag ttggtagctc ttgatccggc aaacaaacca     600
ccgctggtag cggtggtttt tttgtttgca agcagcagat tacgcgcaga aaaaaaggat     660
ctcaagaaga tcctttgatc ttttctacct cgaccgtgag gctccggtgc ccgtcagtgg     720
gcagagcgca catcgcccac agtccccgag aagttggggg gaggggtcgg caattgaacc     780
ggtgcctaga gaaagtggcg cggggtaaac tgggaaagtg atgtcgtgta ctggctccgc     840
cttttccccg agggtgggg agaaccgtat ataagtgcag tagtcgccgt gaacgttctt     900
tttcgcaacg ggttttgccgc cagaacacag gtaagtgccg tgtgtggttc ccgcgggcct     960
ggcctcttta cgggttatgg cccttgcgtg ccttgaatta cttccacgcc cctggctgca    1020
gtacgtgatt cttgatcccg agcttcgggt tggaagtggg tgggagagtt cgaggccttg    1080
cgcttaagga gccccttcgc ctcgtgcttg agttgaggcc tggcctaggc gctggggccg    1140
ccgcgtgcga atctggtggc accttcgcgc ctgtctcgct gctttcgata agtctctagc    1200
catttaaaat ttttgatgac ctgctgcgac gctttttttc tggcaagata gtcttgtaaa    1260
tgcgggccaa gatctgcaca ctggtatttc ggtttttggg gccgcgggcg gcgacggggc    1320
ccgtgcgtcc cagcgcacat gttcggcgag gcggggcctg cgagcgcggc caccgagaat    1380
cggacggggg tagtctcaag ctggccggcc tgctctggtg cctggcctcg cgccgccgtg    1440
```

```
tatcgccccg ccctgggcgg caaggctggc ccggtcggca ccagttgcgt gagcggaaag   1500
atggccgctt cccggccctg ctgcagggag ctcaaaatgg aggacgcggc gctcgggaga   1560
gcgggcgggt gagtcacccg cacaaaggaa aagggccttt ccgtcctcag ccgtcgcttc   1620
atgtgactcc acggagtacc gggcgccgtc caggcacctc gattagttct cgagcttttg   1680
gagtacgtcg tctttaggtt gggggagggg gttttatgcg atggagtttc cccacactga   1740
gtgggtggag actgaagtta ggccagcttg gcacttgatg taattctcct tggaatttgc   1800 ccttttgag tttggatctt ggttcattct caagcctcag acagtggttc aaagtttttt   1860
tcttccattt caggtgtcgt gaaaactacc cctaaaagcc aggatccgat atcgtcgaca   1920
agcttggtac ctccggagcg gccgctctag agctagcgac gtcgaattcc ctgtgacccc   1980
tccccagtgc ctctcctggc cctggaagtt gccactccag tgcccaccag ccttgtccta   2040
ataaaattaa gttgcatcat tttgtctgac taggtgtcct tctataatat tatggggtgg   2100
aggggggtgg tatggagcaa ggggcaagtt gggaagacaa cctgtagggc ctgcggggtc   2160
tattgggaac caagctggag tgcagtggca caatcttggc tcactgcaat ctccgcctcc   2220
tgggttcaag cgattctcct gcctcagcct cccgagttgt tgggattcca ggcatgcatg   2280
accaggctca gctaattttt gttttttttgg tagagacggg gtttcaccat attggccagg   2340
ctggtctcca actcctaatc tcaggtgatc tacccacctt ggcctcccaa attgctggga   2400
ttacaggcgt gaaccactgc tcccttccct gtccttacgc gtagaattgg taaagagagt   2460
cgtgtaaaat atcgagttcg cacatcttgt tgtctgatta ttgattttttg gcgaaaccat   2520 ttgatcatat gacaagatgt gtatctacct taacttaatg attttgataa aaatcattaa   2580
ctagtccatg g                                                       2591

<210> SEQ ID NO 2
<211> LENGTH: 609
<212> TYPE: DNA
<213> ORGANISM: Homo Sapiens

<400> SEQUENCE: 2
atgtgtgctg ctcggctagc ggcggcggcg gcggcggccc agtcggtgta tgccttctcg     60
gcgcgcccgc tggccggcgg ggagcctgtg agcctgggct ccctgcgggg caaggtacta    120
cttatcgaga atgtggcgtc cctctgaggc accacggtcc gggactacac ccagatgaac    180
gagctgcagc ggcgcctcgg accccggggc ctggtggtgc tcggcttccc gtgcaaccag    240
tttgggcatc aggagaacgc caagaacgaa gagattctga attccctcaa gtacgtccgg    300
cctggtggtg ggttcgagcc caacttcatg ctcttcgaga agtgcgaggt gaacggtgcg    360
ggggcgcacc ctctcttcgc cttcctgcgg gaggccctgc cagctcccag cgacgacgcc    420
accgcgctta tgaccgaccc caagctcatc acctggtctc cggtgtgtcg caacgatgtt    480
gcctggaact ttgagaagtt cctggtgggc cctgacggtg tgccccctacg caggtacagc    540 cgccgcttcc agaccattga catcgagcct gacatcgaag ccctgctgtc tcaagggccc    600
agctgtgcc                                                            609

<210> SEQ ID NO 3
<211> LENGTH: 42
<212> TYPE: DNA
<213> ORGANISM: Artificial Sequence
<220> FEATURE:
<223> OTHER INFORMATION: Oligonucleotide UCori-Bam

<400> SEQUENCE: 3
```
ggatccagat ctactcgagg tagaaaagat caaaggatct tc          42

<210> SEQ ID NO 4
<211> LENGTH: 31
<212> TYPE: DNA
<213> ORGANISM: Artificial Sequence
<220> FEATURE:
<223> OTHER INFORMATION: Oligonucleotide UCori-Nco

<400> SEQUENCE: 4
agtccatgga taacgcagga aagaacatgt g                      31

<210> SEQ ID NO 5
<211> LENGTH: 31
<212> TYPE: DNA
<213> ORGANISM: Artificial Sequence
<220> FEATURE:
<223> OTHER INFORMATION: Oligonucleotide hGH-F

<400> SEQUENCE: 5
aggatccgaa ttccctgtga ccccctcccca g                     31

<210> SEQ ID NO 6
<211> LENGTH: 40
<212> TYPE: DNA
<213> ORGANISM: Artificial Sequence
<220> FEATURE:
<223> OTHER INFORMATION: Oligonucleotide hGH-R

<400> SEQUENCE: 6
ctctttacca attctacgcg taaggacagg gaagggagca              40

<210> SEQ ID NO 7
<211> LENGTH: 40
<212> TYPE: DNA
<213> ORGANISM: Artificial Sequence
<220> FEATURE:
<223> OTHER INFORMATION: Oligonucleotide RO-F

<400> SEQUENCE: 7
cttccctgtc cttacgcgta gaattggtaa agagagtcgt              40

<210> SEQ ID NO 8
<211> LENGTH: 41
<212> TYPE: DNA
<213> ORGANISM: Artificial Sequence
<220> FEATURE:
<223> OTHER INFORMATION: Oligonucleotide RO-R

<400> SEQUENCE: 8
ccgtagaaaa ctagttaatg atttttatca aaatcattaa g            41

<210> SEQ ID NO 9
<211> LENGTH: 49
<212> TYPE: DNA
<213> ORGANISM: Artificial Sequence
<220> FEATURE:
<223> OTHER INFORMATION: Oligonucleotide RO-1

<400> SEQUENCE: 9
gaattggtaa agagagtcgt gtaaaatatc gagttcgcac atcttgttg    49

<210> SEQ ID NO 10
<211> LENGTH: 47
<212> TYPE: DNA

<213> ORGANISM: Artificial Sequence
<220> FEATURE:
<223> OTHER INFORMATION: Oligonucleotide RO-2

<400> SEQUENCE: 10
gatttttggc gaaaccattt gatcatatga caagatgtgt atctacc    47

<210> SEQ ID NO 11
<211> LENGTH: 47
<212> TYPE: DNA
<213> ORGANISM: Artificial Sequence
<220> FEATURE:
<223> OTHER INFORMATION: Oligonucleotide RO-3

<400> SEQUENCE: 11
atgattttta tcaaaatcat taagttaagg tagatacaca tcttgtc    47

<210> SEQ ID NO 12
<211> LENGTH: 34
<212> TYPE: DNA
<213> ORGANISM: Artificial Sequence
<220> FEATURE:
<223> OTHER INFORMATION: Oligonucleotide Kan-F

<400> SEQUENCE: 12
aaatcattaa ctagttttct acggggtctg acgc    34

<210> SEQ ID NO 13
<211> LENGTH: 33
<212> TYPE: DNA
<213> ORGANISM: Artificial Sequence
<220> FEATURE:
<223> OTHER INFORMATION: Oligonucleotide Kan-R

<400> SEQUENCE: 13
cagccatgga ctagtggtgg cacttttcgg gga    33

<210> SEQ ID NO 14
<211> LENGTH: 30
<212> TYPE: DNA
<213> ORGANISM: Artificial Sequence
<220> FEATURE:
<223> OTHER INFORMATION: Oligonucleotide MCS1

<400> SEQUENCE: 14
gatccgatat cgtcgacaag cttggtacct    30

<210> SEQ ID NO 15
<211> LENGTH: 20
<212> TYPE: DNA
<213> ORGANISM: Artificial Sequence
<220> FEATURE:
<223> OTHER INFORMATION: Oligonucleotide MCS2

<400> SEQUENCE: 15
caagcttgtc gacgatatcg    20

<210> SEQ ID NO 16
<211> LENGTH: 32
<212> TYPE: DNA
<213> ORGANISM: Artificial Sequence
<220> FEATURE:
<223> OTHER INFORMATION: Oligonucleotide MCS3

<400> SEQUENCE: 16
ccggagcggc cgctctagag ctagcgacgt cg    32

<210> SEQ ID NO 17
<211> LENGTH: 42
<212> TYPE: DNA
<213> ORGANISM: Artificial Sequence
<220> FEATURE:
<223> OTHER INFORMATION: Oligonucleotide MCS3

<400> SEQUENCE: 17
aattcgacgt cgctagctct agagcggccg ctccggaggt ac        42

<210> SEQ ID NO 18
<211> LENGTH: 25
<212> TYPE: DNA
<213> ORGANISM: Artificial Sequence
<220> FEATURE:
<223> OTHER INFORMATION: Oligonucleotide EF1-Xho

<400> SEQUENCE: 18
atctcgagcg tgaggctccg gtgcc        25

<210> SEQ ID NO 19
<211> LENGTH: 29
<212> TYPE: DNA
<213> ORGANISM: Artificial Sequence
<220> FEATURE:
<223> OTHER INFORMATION: Oligonucleotide EF1-R

<400> SEQUENCE: 19
tcggatcctg gcttttaggg gtagttttc        29

<210> SEQ ID NO 20
<211> LENGTH: 18
<212> TYPE: DNA
<213> ORGANISM: Artificial Sequence
<220> FEATURE:
<223> OTHER INFORMATION: Oligonucleotide MVGFP-F

<400> SEQUENCE: 20
gggatccacc ggtcgcca        18

<210> SEQ ID NO 21
<211> LENGTH: 29
<212> TYPE: DNA
<213> ORGANISM: Artificial Sequence
<220> FEATURE:
<223> OTHER INFORMATION: Oligonucleotide MVGFP-R

<400> SEQUENCE: 21
atagaattct tacttgtaca gctcgtcca        29

<210> SEQ ID NO 22
<211> LENGTH: 23
<212> TYPE: DNA
<213> ORGANISM: Artificial Sequence
<220> FEATURE:
<223> OTHER INFORMATION: Oligonucleotide GPX1-F

<400> SEQUENCE: 22
gggatccatg tgtgctgctc ggc        23

<210> SEQ ID NO 23
<211> LENGTH: 27
<212> TYPE: DNA
<213> ORGANISM: Artificial Sequence
<220> FEATURE:

<223> OTHER INFORMATION: Oligonucleotide GPX1-R

<400> SEQUENCE: 23
atagaattct taggcacagc tgggatt                                27

<210> SEQ ID NO 24
<211> LENGTH: 19
<212> TYPE: DNA
<213> ORGANISM: Artificial Sequence
<220> FEATURE:
<223> OTHER INFORMATION: Oligonucleotide LHA-F

<400> SEQUENCE: 24
gctgacgctg caggtgatc                                         19

<210> SEQ ID NO 25
<211> LENGTH: 38
<212> TYPE: DNA
<213> ORGANISM: Artificial Sequence
<220> FEATURE:
<223> OTHER INFORMATION: Oligonucleotide LHA-R

<400> SEQUENCE: 25
gacaagatgt gtgtctaccg cttcaggtta cccgccag                    38

<210> SEQ ID NO 26
<211> LENGTH: 39
<212> TYPE: DNA
<213> ORGANISM: Artificial Sequence
<220> FEATURE:
<223> OTHER INFORMATION: Oligonucleotide RHA-F

<400> SEQUENCE: 26
tggcagggcg gggcgtaact acgcctctgt tcgtctcga                   39

<210> SEQ ID NO 27
<211> LENGTH: 20
<212> TYPE: DNA
<213> ORGANISM: Artificial Sequence
<220> FEATURE:
<223> OTHER INFORMATION: Oligonucleotide RHA-R

<400> SEQUENCE: 27
ctcagcagca actcacgtac                                        20

<210> SEQ ID NO 28
<211> LENGTH: 38
<212> TYPE: DNA
<213> ORGANISM: Artificial Sequence
<220> FEATURE:
<223> OTHER INFORMATION: Oligonucleotide IN-F

<400> SEQUENCE: 28
ctggcgggta acctgaagcg gtagacacac atcttgtc                    38

<210> SEQ ID NO 29
<211> LENGTH: 42
<212> TYPE: DNA
<213> ORGANISM: Artificial Sequence
<220> FEATURE:
<223> OTHER INFORMATION: Oligonucleotide IN-1

<400> SEQUENCE: 29
atttttggcg aaaccattct atcatatgac aagatgtgtg tc               42

```
<210> SEQ ID NO 30
<211> LENGTH: 42
<212> TYPE: DNA
<213> ORGANISM: Artificial Sequence
<220> FEATURE:
<223> OTHER INFORMATION: Oligonucleotide IN-2

<400> SEQUENCE: 30
atatgataga atggtttcgc caaaaatcaa taatcagaca ac                            42

<210> SEQ ID NO 31
<211> LENGTH: 37
<212> TYPE: DNA
<213> ORGANISM: Artificial Sequence
<220> FEATURE:
<223> OTHER INFORMATION: Oligonucleotide IN-R

<400> SEQUENCE: 31
caaacttttt gatgttcatc ttgttgtctg attattg                                  37

<210> SEQ ID NO 32
<211> LENGTH: 37
<212> TYPE: DNA
<213> ORGANISM: Artificial Sequence
<220> FEATURE:
<223> OTHER INFORMATION: Oligonucleotide SACB-F

<400> SEQUENCE: 32
caataatcag acaacaagat gaacatcaaa agtttg                                   37

<210> SEQ ID NO 33
<211> LENGTH: 38
<212> TYPE: DNA
<213> ORGANISM: Artificial Sequence
<220> FEATURE:
<223> OTHER INFORMATION: Oligonucleotide SACB-R

<400> SEQUENCE: 33
cttacgtgcc gatcattatt tgttaactgt taattgtc                                 38

<210> SEQ ID NO 34
<211> LENGTH: 39
<212> TYPE: DNA
<213> ORGANISM: Artificial Sequence
<220> FEATURE:
<223> OTHER INFORMATION: Oligonucleotide CATR-F

<400> SEQUENCE: 34
caattaacag ttaacaaata atgatcggca cgtaagagg                                39

<210> SEQ ID NO 35
<211> LENGTH: 39
<212> TYPE: DNA
<213> ORGANISM: Artificial Sequence
<220> FEATURE:
<223> OTHER INFORMATION: Oligonucleotide CATR-R

<400> SEQUENCE: 35
cgagacgaac agaggcgtag ttacgccccg ccctgccac                                39

<210> SEQ ID NO 36
<211> LENGTH: 21
<212> TYPE: DNA
<213> ORGANISM: Artificial Sequence
<220> FEATURE:
<223> OTHER INFORMATION: Oligonucleotide GPX1-sF
```

```
<400> SEQUENCE: 36
ggcaccacgg tccgggacta c                                               21

<210> SEQ ID NO 37
<211> LENGTH: 21
<212> TYPE: DNA
<213> ORGANISM: Artificial Sequence
<220> FEATURE:
<223> OTHER INFORMATION: Oligonucleotide GPX1-sR

<400> SEQUENCE: 37
cagggcctcc cgcaggaagg c                                               21
```